United States Patent
Patel

(10) Patent No.: US 10,741,275 B2
(45) Date of Patent: Aug. 11, 2020

(54) MEDICINE DISPENSING SYSTEM WITH FEEDBACK PRE-FILL APPARATUS

(71) Applicant: Miteshkumar Ishwarbhai Patel, San Leandro, CA (US)

(72) Inventor: Miteshkumar Ishwarbhai Patel, San Leandro, CA (US)

(73) Assignee: DOSEPACK CORPORATION

( * ) Notice: Subject to any disclaimer, the term of this patent is extended or adjusted under 35 U.S.C. 154(b) by 229 days.

(21) Appl. No.: 15/704,056

(22) Filed: Sep. 14, 2017

(65) Prior Publication Data

US 2019/0080790 A1     Mar. 14, 2019

(51) Int. Cl.

| | |
|---|---|
| *G16H 20/13* | (2018.01) |
| *G07F 17/00* | (2006.01) |
| *G06F 16/2457* | (2019.01) |
| *G07F 11/44* | (2006.01) |
| *G07F 11/62* | (2006.01) |
| *G16H 10/60* | (2018.01) |
| *G07F 11/10* | (2006.01) |
| *B65B 57/06* | (2006.01) |

(Continued)

(52) U.S. Cl.
CPC ....... *G16H 20/13* (2018.01); *G06F 16/24575* (2019.01); *G07F 11/10* (2013.01); *G07F 11/44* (2013.01); *G07F 11/62* (2013.01); *G07F 17/0092* (2013.01); *G16H 10/60* (2018.01); *B65B 5/103* (2013.01); *B65B 57/02* (2013.01); *B65B 57/06* (2013.01)

(58) Field of Classification Search
CPC .... G06F 16/24575; G07F 11/10; G07F 11/44; G07F 11/62; G07F 17/0092; G16H 10/60; G16H 20/13; A61J 7/0084; B65B 5/103; B65B 57/02; B65B 57/06
USPC ...................... 53/473, 246, 154, 167, 64, 67
See application file for complete search history.

(56) References Cited

U.S. PATENT DOCUMENTS

| | | | | |
|---|---|---|---|---|
| 1,562,152 A | * | 11/1925 | Du Grenier | ............. G07F 11/44 221/263 |
| 3,036,703 A | * | 5/1962 | Menolasino | ........ G07F 17/0092 206/303 |

(Continued)

*Primary Examiner* — Robert F Long
*Assistant Examiner* — Eduardo R Ferrero
(74) *Attorney, Agent, or Firm* — Firasat Ali; Creso Legal

(57) ABSTRACT

The medicine dispensing system includes a plurality of storage containers for storing medical pills. The system also includes a hopper, a top and a bottom pre-fill tray, and a packing plate that are placed underneath each other respectively. Both the top and bottom pre-fill trays include a plurality of X-direction and Y-direction pointers.
The system also includes a control module that uses feedback logic to align the top pre-fill tray with the bottom pre-fill tray using the X and Y direction pointers.
In operation, the medicine dispensing system controls dispensing and navigation of pills from the storage container through the hopper, into the top pre-fill tray, into the bottom pre-fill tray, into the packing plate, and ultimately into a desired slot in the pill pack.
The top and bottom pre-fill trays provide for separated compartmentalization of pills. This allows the medical pill dispensing system to parallel process and dispense pills designated for multiple pill packs at the same time without having to wait till the completion of any one pill pack. The separated compartmentalization ensures pills designated for one pill pack are not mixed with pills designated for another pill pack.

9 Claims, 16 Drawing Sheets

(51) Int. Cl.
 *B65B 57/02* (2006.01)
 *B65B 5/10* (2006.01)

(56) References Cited

U.S. PATENT DOCUMENTS

| | | | | |
|---|---|---|---|---|
| 3,878,967 | A * | 4/1975 | Joslin | G06Q 20/342 221/88 |
| 3,917,045 | A * | 11/1975 | Williams | A61J 7/0481 194/210 |
| 4,546,901 | A * | 10/1985 | Buttarazzi | G07F 17/0092 221/10 |
| 4,660,991 | A * | 4/1987 | Simon | G04B 37/127 368/10 |
| 4,678,894 | A * | 7/1987 | Shafer | B01L 9/56 235/375 |
| 5,010,929 | A * | 4/1991 | Tisma | B65B 39/14 141/1 |
| 5,014,851 | A * | 5/1991 | Wick | A61J 1/035 206/461 |
| 6,170,230 | B1 * | 1/2001 | Chudy | B65B 5/103 53/168 |
| 6,370,841 | B1 * | 4/2002 | Chudy | B65B 5/103 53/411 |
| 6,611,733 | B1 * | 8/2003 | De La Huerga | A61J 1/1437 700/236 |
| 7,277,776 | B2 * | 10/2007 | Kim | B65B 5/103 700/231 |
| 7,779,614 | B1 * | 8/2010 | McGonagle | A61J 1/035 53/238 |
| 7,950,202 | B2 * | 5/2011 | Kodama | B65B 5/103 53/244 |
| 7,958,701 | B2 * | 6/2011 | Knoth | B65B 5/103 221/121 |
| 8,200,366 | B2 * | 6/2012 | Ali | G06F 19/3462 700/240 |
| 8,584,434 | B2 * | 11/2013 | Kodama | B65B 5/103 53/235 |
| 2001/0001358 | A1 * | 5/2001 | Yuyama | B65B 5/103 53/131.2 |
| 2002/0103573 | A1 * | 8/2002 | Fellows | G07F 11/54 700/240 |
| 2002/0148861 | A1 * | 10/2002 | Koehler | G07F 17/0092 222/485 |
| 2002/0179619 | A1 * | 12/2002 | Geltser | A61J 7/02 221/2 |
| 2003/0057230 | A1 * | 3/2003 | Stevens | B65B 5/103 221/200 |
| 2003/0057231 | A1 * | 3/2003 | Kim | B65B 5/103 221/263 |
| 2004/0065053 | A1 * | 4/2004 | Rice | B65B 5/103 53/445 |
| 2004/0074916 | A1 * | 4/2004 | Priebe | A61J 7/02 221/289 |
| 2004/0094564 | A1 * | 5/2004 | Papp | A61J 7/0084 221/25 |
| 2005/0087473 | A1 * | 4/2005 | Fabricius | A61J 1/035 206/534 |
| 2005/0263537 | A1 * | 12/2005 | Gerold | G07F 11/44 221/124 |
| 2006/0058917 | A1 * | 3/2006 | Vonk | A61J 7/0481 700/236 |
| 2006/0129273 | A1 * | 6/2006 | Kirsch | G07F 9/026 700/231 |
| 2006/0259188 | A1 * | 11/2006 | Berg | A61J 7/0084 700/231 |
| 2006/0273106 | A1 * | 12/2006 | Kim | B65B 5/103 221/200 |
| 2007/0185615 | A1 * | 8/2007 | Bossi | G06F 19/3462 700/244 |
| 2008/0190076 | A1 * | 8/2008 | Klingel | B65B 57/06 53/493 |
| 2009/0050444 | A1 * | 2/2009 | Yuyama | B65G 65/00 198/347.1 |
| 2009/0084807 | A1 * | 4/2009 | Fitzgerald | B65G 1/04 221/1 |
| 2009/0188937 | A1 * | 7/2009 | Kim | A61J 7/0069 221/312 B |
| 2009/0277815 | A1 * | 11/2009 | Kohl | A61J 7/0481 206/531 |
| 2009/0281657 | A1 * | 11/2009 | Gak | A61J 7/0481 700/242 |
| 2010/0249997 | A1 * | 9/2010 | Greyshock | G07F 11/54 700/240 |
| 2011/0245969 | A1 * | 10/2011 | Monto | G07F 9/026 700/240 |
| 2012/0004770 | A1 * | 1/2012 | Ooyen | G07F 11/58 700/235 |
| 2013/0018503 | A1 * | 1/2013 | Carson | B65B 57/16 700/216 |
| 2013/0153594 | A1 * | 6/2013 | Yuyama | G07F 11/42 221/1 |
| 2013/0270291 | A1 * | 10/2013 | Omura | B65D 83/04 221/92 |
| 2013/0282163 | A1 * | 10/2013 | Brown | G07F 17/0092 700/215 |
| 2013/0340390 | A1 * | 12/2013 | Carson | B25J 9/0096 53/411 |
| 2014/0261881 | A1 * | 9/2014 | Chudy | A61J 7/0084 141/94 |
| 2014/0367301 | A1 * | 12/2014 | Kim | B65B 5/08 206/534 |
| 2015/0066204 | A1 * | 3/2015 | Patel | G06F 19/3462 700/232 |
| 2015/0066206 | A1 * | 3/2015 | Patel | G06F 19/3462 700/235 |
| 2015/0196445 | A1 * | 7/2015 | Larkner | G06Q 10/087 312/209 |
| 2015/0290084 | A1 * | 10/2015 | Kim | A61J 7/0069 221/1 |
| 2016/0075460 | A1 * | 3/2016 | Despa | G07F 17/0092 700/240 |
| 2017/0217619 | A1 * | 8/2017 | Hellenbrand | B65B 35/30 |

* cited by examiner

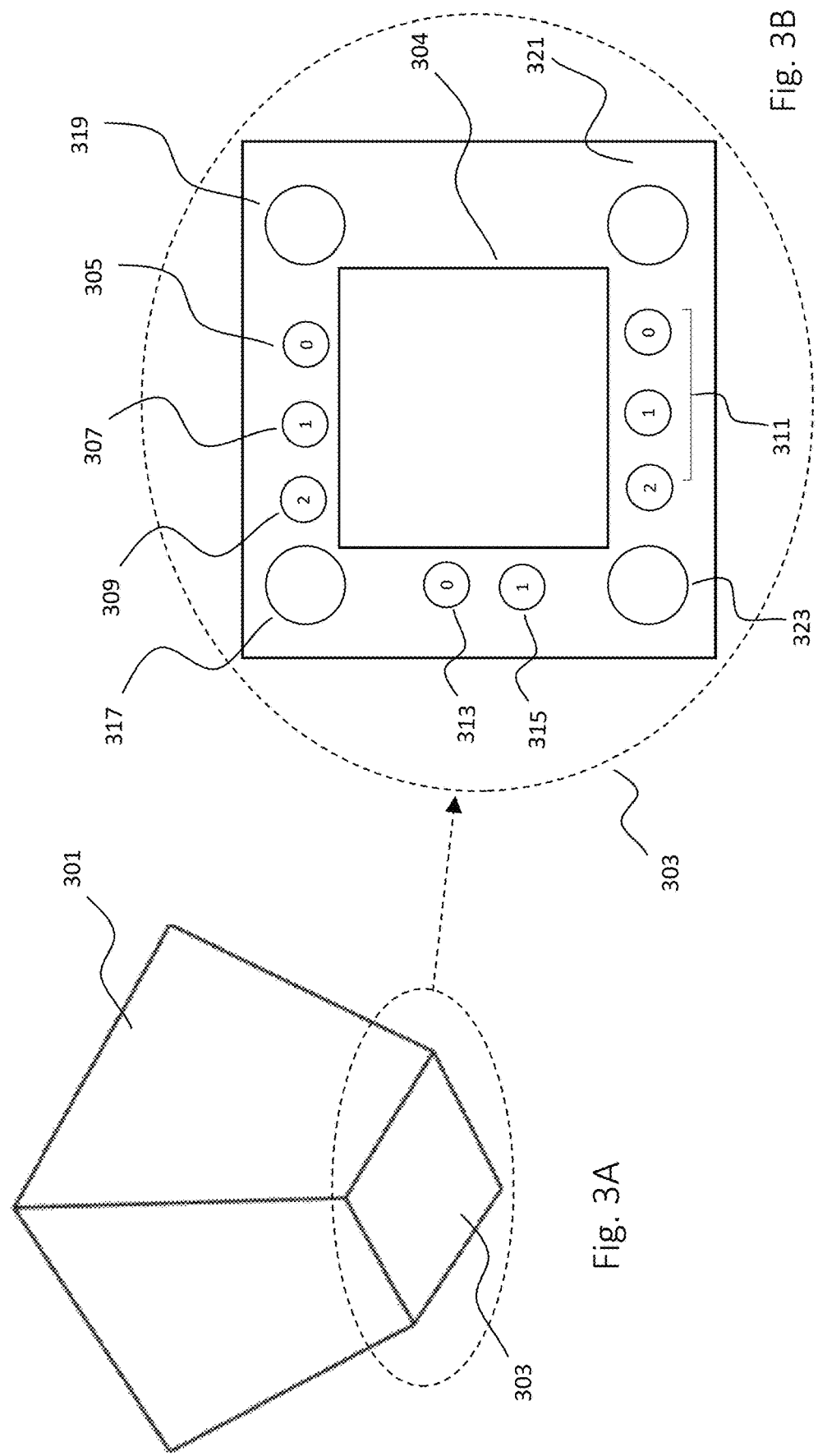

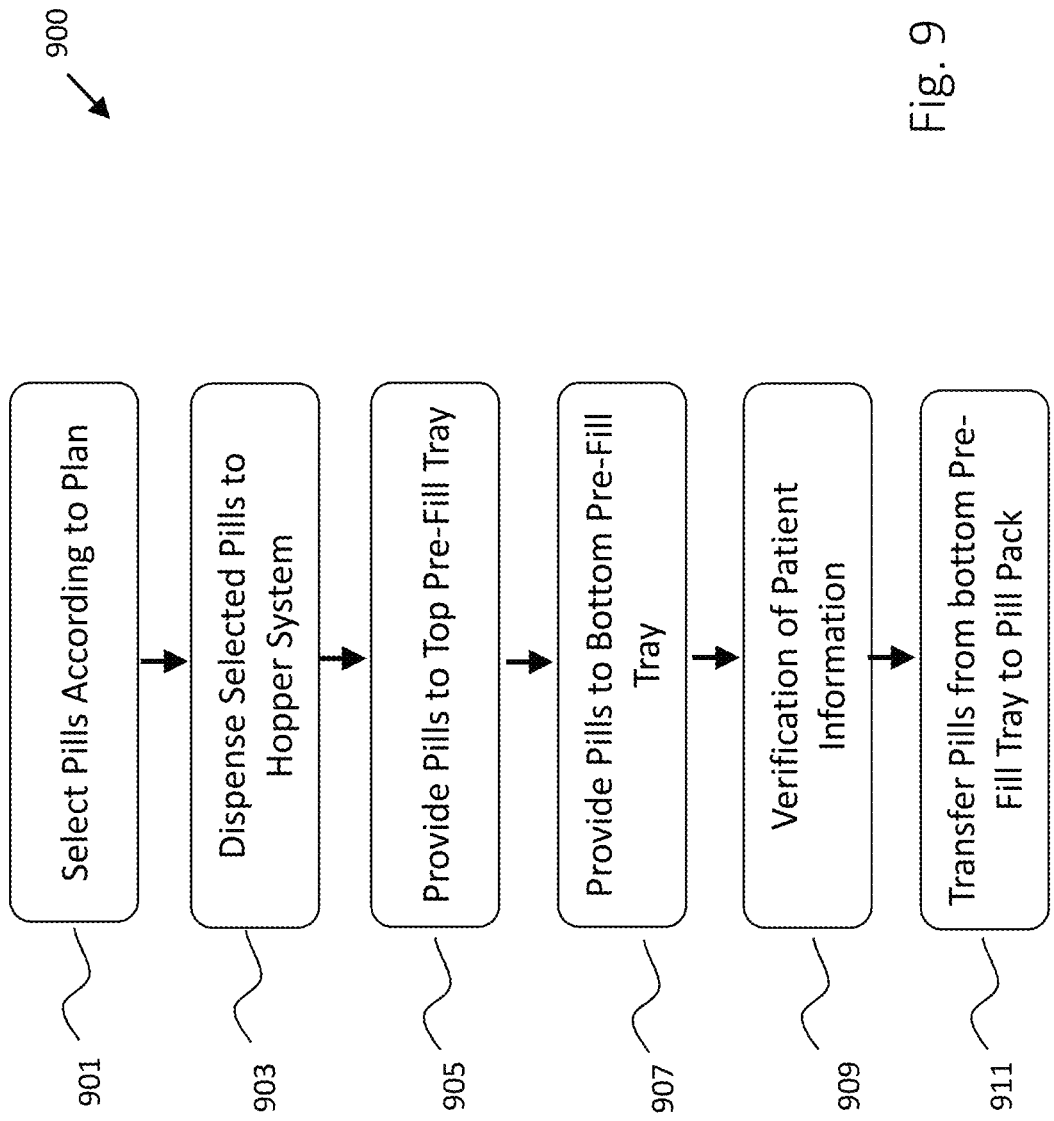

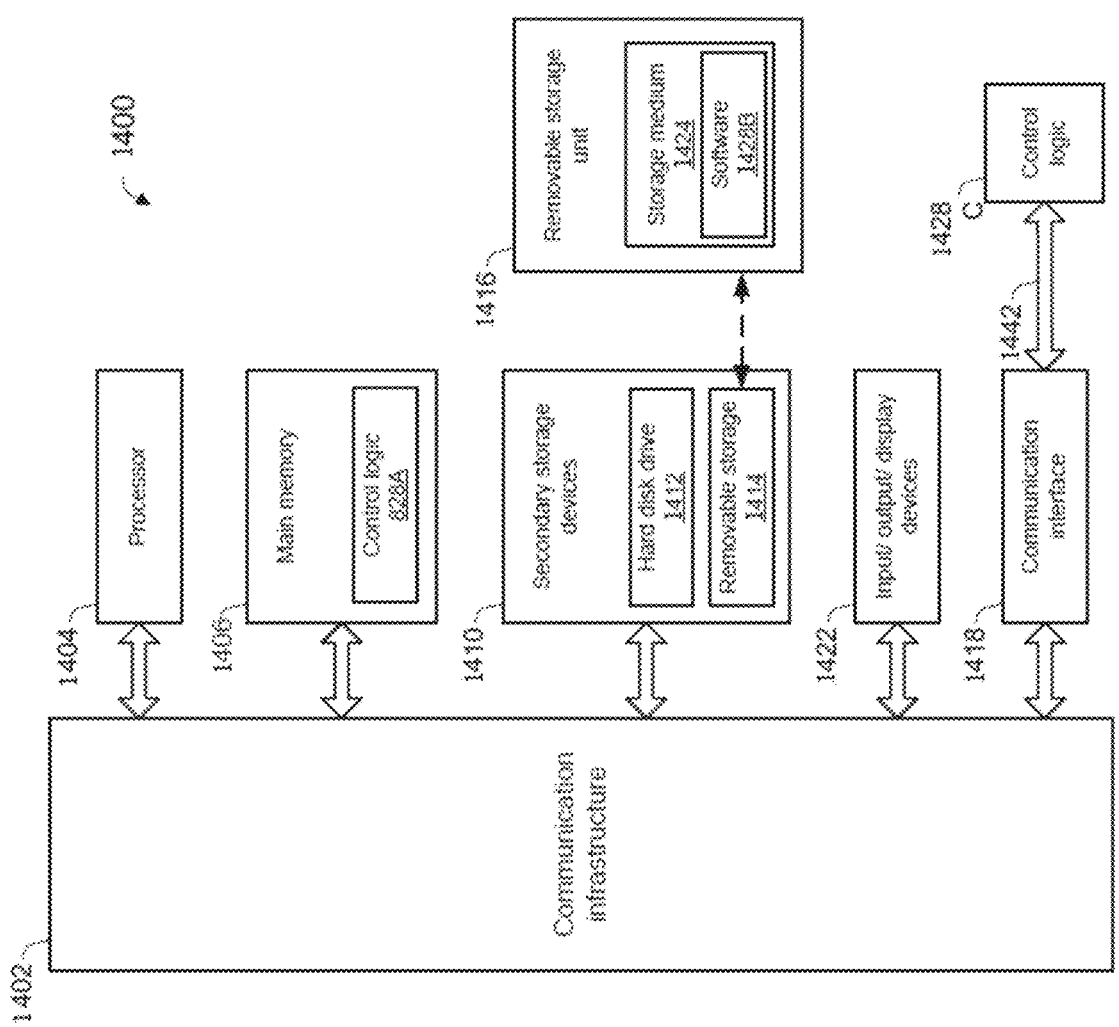

MEDICINE DISPENSING SYSTEM WITH FEEDBACK PRE-FILL APPARATUS

This application is a continuation-in-part of an application Ser. No. 14/155,873, titled "MEDICAL PILL DISPENSING SYSTEM," filed on Jan. 15, 2014, having Miteshkumar Ishwarbhai Patel, Feros Khan Seyed Yousuf Khan, and Sergey Shkapov as inventors, which is a continuation-in-part of an application Ser. No. 14/018,245, filed on Sep. 4, 2013, titled "MEDICATION DOSAGE DISPENSING SYSTEM AND METHODS HAVING CUSTOMIZATION AND MODIFICATION FOR MEDICINE DISPENSING CONFIGURATIONS," having Miteshkumar Ishwarbhai Patel and Hemang Vipimchandra Trivedi as inventors. Application Ser. No. 14/018,245 and Ser. No. 14/155,873 are also incorporated herein by reference.

BACKGROUND OF THE INVENTION

Field of the Invention

This application is related to automated medical pill dispensers, and more particularly, to medical pill dispensers having a feedback pre-fill apparatus.

Description of the Related Art

Individuals with long-term medical issues, or even shorter term medical needs, take various medications each day to maintain or improve their medical condition. Individuals with more than one medical condition may take several pills daily and in some instances, may take upwards of 10 or more pills a day, i.e., about 70 or more pills a week.

The medications, i.e. tablets, capsules, or pills, are typically diagnosed by a doctor to be taken with a certain regimen during the course of the day, including with several restrictions such as to be taken before food, during a meal, or after food, or even to wait a certain period of time after having a meal. Regimens may vary drastically from one pill to another and may include taking a certain pill twice a day or another pill only at bed time. As such, managing a complex pill taking schedule become cumbersome causing individuals to mistakenly take the wrong pill at the wrong time or entirely miss taking a certain pill within the required time frame.

To alleviate the management of complex pill taking schedules, pharmacies and other companies have made pill packs having several chambers where each chamber would be allocated for a certain time, such as morning, afternoon, and night, and additionally provided instructions for the regimen to be followed. These pill packs have been typically manually filled by pharmacies and in recent years companies have developed automated systems to address the large volume of pill dispensing while providing proper regimen instructions.

For example, automated systems for dispensing pills according to a pre-programmed schedule are used today. Many such pill dispensers dispense different dosages of different pills at different frequencies and therefore at different times. Some pill dispensers have multiple pill chambers dispense pills contained within the chambers resulting in having only a single pill in each chamber with an allocated time such that the pill taker takes the medications in the designated chamber at the appointed time, e.g. afternoon. However, several drawbacks exist in these systems, including the need for manual user input. Some of these drawbacks were discussed and addressed in the earlier patent bearing patent application Ser. No. 14/155,873 for a Medical Pill Dispensing System.

One of the drawbacks in current automated pill dispensing systems is the time consumed in filling each pill pack. Since a pill pack may contain a chamber for each day of the week and possibly a chamber for 3 or 4 times during the day, e.g. morning, afternoon, night, and bed-time, a pill pack may contain a total of 28 chambers. Current automated system drops each pill from its source into the pill pack while packaging one pill per chamber at a time. Until each chamber is packed with its single pill, the automated systems would not dispense the next pill that is allocated for the next chamber in the pill pack. The wait causes undue delay and results in an inefficient process.

The current systems are also inefficient when it comes to packaging more than one pill pack. In addition to the inefficiency noted above, the current systems can only complete one pill pack at a time. If they are to fill a second pill pack, the current systems can only turn to the second pill pack only upon completion of the first pill pack thereby causing queuing and delay problems in packaging multiple pill packs.

Yet another drawback in the current automated system is the inability to populate more than a single pill in each chamber and also dispense more than one pill at a time due to need to wait for the first chamber to be filled before the system can move to the second chamber. The drawback results in filling several pill packs with a single pill for each chamber until the entire pill taking regimen for a patient is satisfied. For example, if a pill pack of 28 chambers is used, where each chamber is capable of receiving a single pill in each chamber, then a patient taking over 70 pills would need at least two or more pills packs that would take up more volume for storage. As such, an efficient and automated medication system that overcomes these drawbacks is needed.

BRIEF DESCRIPTION OF THE DRAWINGS

The accompanying drawings are included to provide further understanding of the invention and constitute a part of the specification. The drawings listed below illustrate embodiments of the invention and, together with the description, serve to explain the principles of the invention, as disclosed by the claims and their equivalents.

FIG. 3A is a block diagram depicting the details of the hopper system, according to some embodiments.

FIG. 3B is a detailed view of the bottom of the hopper system, according to some embodiments.

FIG. 9 is a flowchart illustrating one method of operation of the pill dispensing robot, according to some embodiments.

FIG. 14 is a block diagram of a computer system that can is used in operation of the pill dispensing robot, according to some embodiments.

Figure 1:
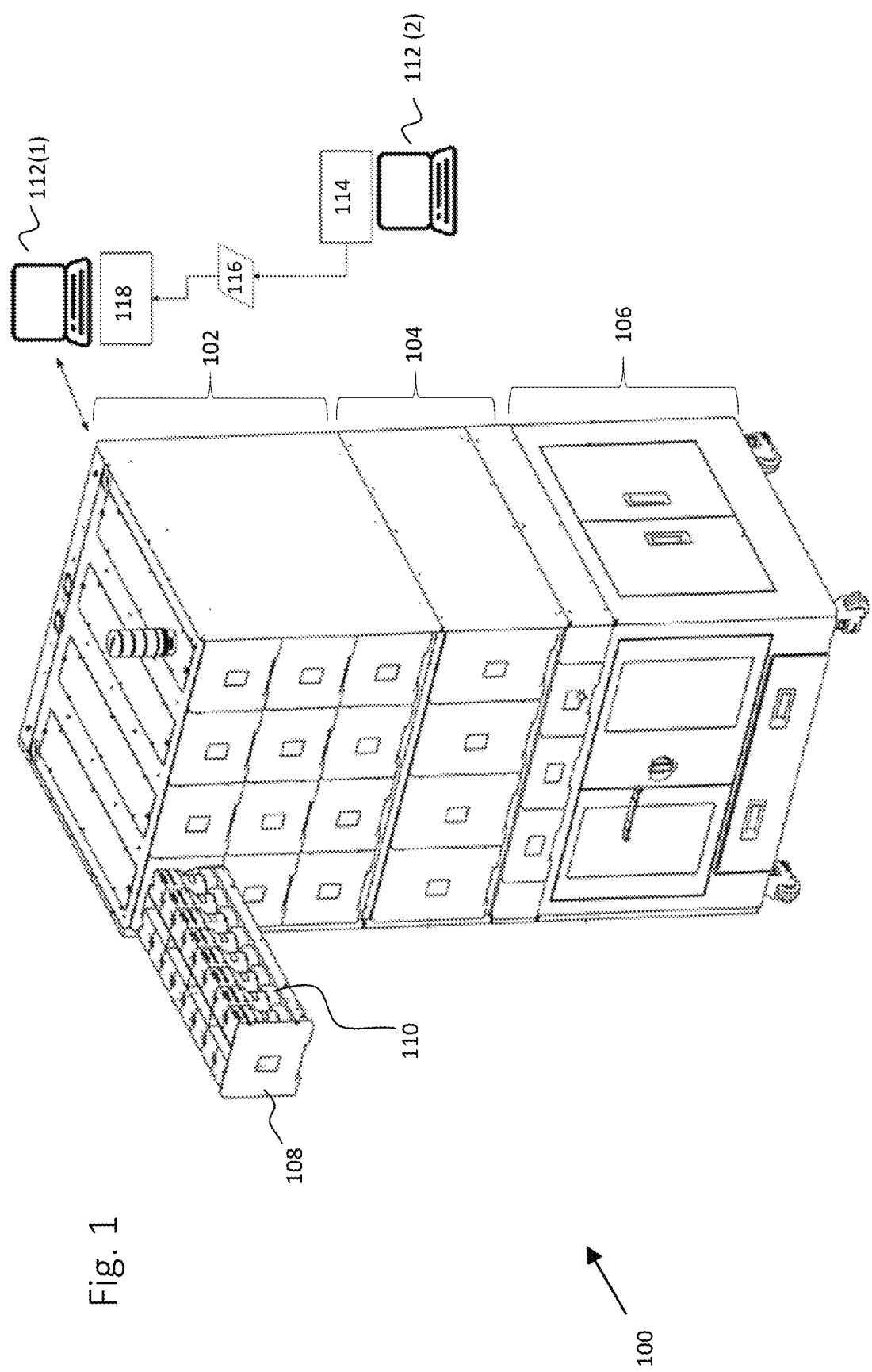
FIG. 1 is a block diagram of a general view of a pill dispensing robot, according to some embodiments.

While the embodiments of the application are susceptible to various modifications and alternative forms, specific embodiments are provided as examples in the drawings and detailed description. It should be understood that the drawings and detailed description are not intended to limit the embodiments to the particular form disclosed. Instead, the intention is to cover all modifications, equivalents and alternatives falling within the spirit and scope of the invention as defined by the appended claims.

DETAILED DESCRIPTION

The automated pill dispensing methods and systems described herein are directed to medical pill dispensers having a feedback pre-fill apparatus. The methods used dispense pills into a plurality of pill packs, wherein each pill pack has multiple slots for each day, which correspond to different times of the day. The pills are dispensed in accordance to a prescription plan and a pill dispensing robot is used for completing the end to end pill dispensing process. The pre-fill apparatuses, which are a part of the pill dispensing robot, allow the filling of a first pill pack while allowing the pill dispensing robot to continue dispensing pills for the second pill pack and not having to stop and wait for the completion of the first pill pack. The continuous dispensing of pills for multiple and separate pill packs allows the pill dispensing robot to attain higher efficiency and complete a higher volume of pills packs while ensuring accuracy that each pill pack contains the correct pills that were designated by the prescription plan.

FIG. 1 is a block diagram of a pill dispensing robot 100, according to one or more embodiments. Particularly, FIG. 1 depicts the outer body of the pill dispensing robot 100. The inner components, i.e. the machine body that resides within the outer body will be described in FIG. 2. The pill dispensing robot ("robot") 100 of FIG. 1 includes a canister drawer section 102, a manual fill tray section 104, and a dispensing section 106.

The canister drawer section 102, includes a plurality of canisters drawers 108 and a canister operation module (not shown). Each canister drawer 108 includes a plurality of canisters 110. Each canister 110 is designed to store medicines, i.e. pills, which are to be dispensed by the robot 100 in accordance with the prescription plan 116 for dispensing. The pills stored in the canister may be of the same type. Each of the plurality of canisters may have a different types and sizes of pills thereby allowing the robot 100 to store several types of pills in the canister drawer section 102.

The manual fill tray section 104 includes a plurality of manual fill trays. These are fills trays that can be populated manually with medicines/pills by the operator of the robot 100. Each fill tray in this manual fill tray section 104 may be used to store a particular type of pill that is not commonly used by the robot.

The dispensing section 106 includes a hopper, a plurality of pre-fill trays, and a packing plate. The hopper is a component of the dispensing section 106 that goes from a wider opening at it top to a narrow opening bottom at it bottom thereby creating a funnel type apparatus. Each pre-fill tray, from the plurality of pre-fill trays, includes a grid of slots. The slots may be of a square shape. Alternatively, the slots may also be of rectangular or other shapes. The packing plate, or pack plate, is designed to accept a plurality of pill packs, also referred to as blister packs. A pill/blister pack is essentially the final pill pack that is used by a patient and includes the pills designated for the patient in accordance with the prescription plan. The packing plate slot is designed to accept a plurality of pill/blister packs. The packing plate locks the pill packs into their position such that they do not move with respect to the packing plate and allow for the dispensing of the pills into them.

Robot 100 also includes a computing device 122(1) for controlling robot 100 operations. Robot 100 can communicate with a computing device 122(2) to receive plans for robot 100 operations. Computing device 122(2) is configured to generate and/or modify plans for operation of robot 100.

Computing device 112(1) and 112(2) can be any type of a personal computer, a server, a mobile device, a personal assistant, and the like, including a device having memory for storing one or more applications and one or more processors. In one embodiment, computing device 112(1) and 112(2) can be implemented using the same computing device.

Computing device 112(2) can execute (e.g., by using the one or more processors) a plan generation module 116 to access, generate, and/or modify a plan 116. Plan 116 indicates a pill distribution by robot 100. Plan 116 is then communicated to a control module 118, which can be executed by computing device 112(1) (e.g., by using one or more processors). Control module 118 processes the plan and controls the robot in accordance with the plan.

Dispensing section 106 is configured to receive pills from canisters 110 placed in the canister drawer 108 as well as manual fill trays that are in the manual fill tray section 104. The control module 118 allows selection of the pills associated with the prescription plan 116 from the respective canisters 110 and manual fill trays. The selected pills are then processed and dispensed, i.e., dropped, into the dispensing section 106. The pills make their way through the hopper and into a first pre-fill tray and then onto the $2^{nd}$ pre-fill tray and finally into the appropriate blister pack that is located in the packing plate.

Various embodiments of using such a control module and plan generation module are described with reference to the Figures below.

Figure 2:
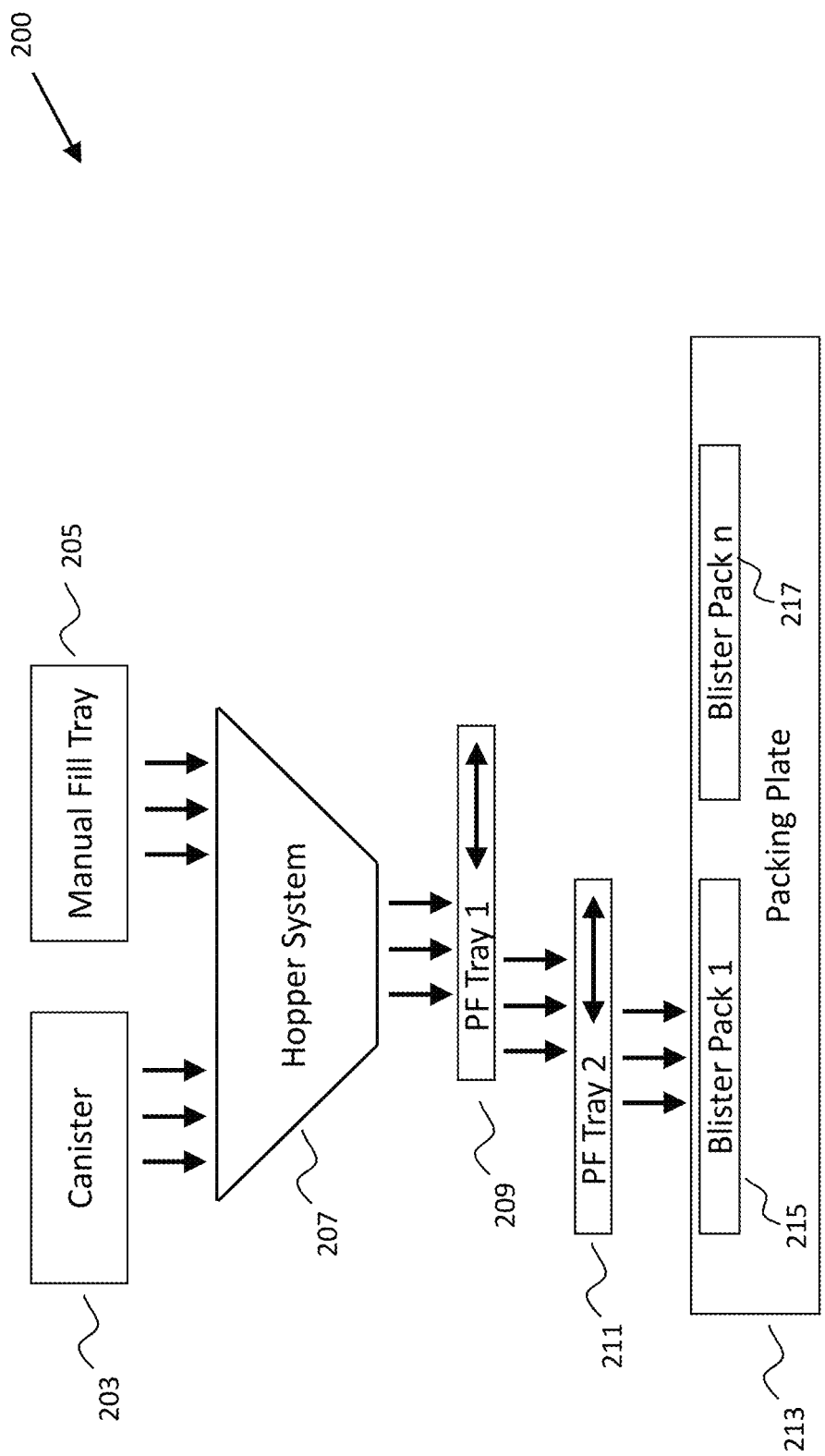
FIG. 2 is a block diagram of some of the components of the machine body of the pill dispensing robot, according to some embodiments.

FIG. 2 is a block diagram of some of the components of the machine body of the pill dispensing robot, according to some embodiments. The inner components 200 described in FIG. 2 reside within the outer body of the pill dispensing robot 100 as shown in FIG. 1.

The upper part of the pill dispensing robot 100 includes a canister drawer section 102. This section includes a plurality of canisters drawers and a plurality of canisters 203 within each canister drawer. The upper part of the pill dispensing robot 100 also includes a manual fill tray section and a plurality of manual fill trays 205 within this section.

The dispensing section 106 includes a hopper 207. The dispensing section 106 also includes a top pre-fill tray 209 and a bottom pre-fill tray 211. Further, a packing plate 213 that includes a plurality of pill packs 215 and 217 are also located in the dispensing section of the robot 100.

The vertical order of arrangement includes canisters 203 and manual fill trays 205 at the top followed by a hopper 207 below it. Alternatively, a small hopper (not shown) can be placed underneath the hopper 207.

The top pre-fill tray 209 is directly underneath the hopper 207 and the bottom pre-fill tray 211 is located underneath the top pre-fill tray 209. Under the bottom pre-fill tray 211 is the packing plate that can hold a plurality of pill packs. Details on the above mentioned components can be found in the figure below.

FIG. 3A is a block diagram depicting the details of the hopper system, according to some embodiments. In one embodiment, the hopper 301 has a wider top and narrower bottom. The inside of the hopper 301 is hollow with a wide opening at the top that allows a pill dispensed from the canister or manual fill tray to enter the hopper and then using gravity drop through its hollow inside and exit the hopper 301 from it narrower opening at the bottom.

The narrower bottom of the hopper 301 that has a narrow opening is square shaped 303. The square shape of at this exit matches the shape of a chamber in the pre-fill tray that would receive the pills dropped from the hopper 301. The exact, or nearly exact, shape match between the hopper's exit and the chamber of the pre-fill tray ensures that the hopper 301 and pre-fill tray's chamber are aligned properly to ensure that pills dropped from the hopper 301 enter directly into the chamber and cannot go anywhere else. Alternatively, the bottom shape of the hopper 301 may be other shapes, such as rectangle, diamond, circle, or any other shape that would match the shape of the chamber in the pre-fill tray resulting in a shape match such that pills dropped enter directly into chamber of pre-fill tray and no pills are displaced due to any shape mismatches.

The hopper 301 may be acrylic and of a clear or a transparent color to allow a user to look into it. Alternatively, other materials and colors are also contemplated. In yet another embodiment, the hopper 301 may also include a square and hollow tunnel extending from the square exit. The tunnel may have a certain calculated height that prevents pills from bouncing back into the hopper 301 when they are dropped into the pre-fill tray.

In another embodiment, the hopper 301 may include a camera. The camera may be used for counting pills dropped from the hopper 301 into the pre-fill tray. The camera may also act as quality assurance to determine the types of pills dropped through the hopper. Alternatively, the hopper may include a photodiode or some light emitting mechanism that is used to calculate the amount of pills dropped through the hopper. Using this method, a light beam, or an array of light beams, may cover the surface area at the bottom exist section 303 of the hopper 301 and the pills dropped may be counted based on the amount of disruption in the light beam(s).

The hopper may also include a drop door that can be located at the narrower bottom exit and the drop door may be controlled by a motor to open and close thereby allowing the pills to drop from the hopper or accumulate the pills until the drop into the chamber of the pre-fill tray.

FIG. 3B is a block diagram depicting a close up and zoomed in view of the bottom narrower square exit 303 of the hopper 301. The square shaped exit 303 at the bottom of the hopper 301 includes a plurality of sensors and an opening 304 at its exit. The sensors determine the X and Y position of the hopper 301 with respect to the top pre-fill tray. The sensors 305, 307, 309 are used for determining the X coordinate position of the hopper 301. The sensors 313 and 315 are used for determining the Y coordinate position of the hopper 301. The X and Y coordinate sensors provide the robot 100 with data on the current location of the hopper that is used by the robot to send commands to the pre-fill tray to move in a particular direction in order to align with the hopper 301. The alignment is needed for the pills to be dropped directly from the hopper 301 accurately into the chamber of a pre-fill tray without any spill over.

In one embodiment, the narrower square exit 303 of the hopper includes a printed circuit board (PCB). The PCB is overlaid over the square exit thereby covering the area between the opening 304 and the edge of the larger square. The sensors may be photo sensors 305, 307, 309, 311, 313, and 315 and may be part of the PCB circuitry placed in the locations as depicted in FIG. 3B.

In one embodiment, the narrower square exit 303 of the hopper 301 includes six X coordinate sensors and two Y coordinate sensors. Alternatively, other combinations of sensors and placement of X coordinate and Y coordinate sensors are also contemplated.

The narrower square exit 303 of the hopper 301 also includes a plurality of corner sensors. These corner sensors 317, 319, 321, and 323 are used for aligning the hopper 301 with the chamber of the pre-fill tray.

Alternatively, as mentioned earlier, the hopper system may include another small hopper that is placed beneath the hopper 301.

Figures 4A, 4B:
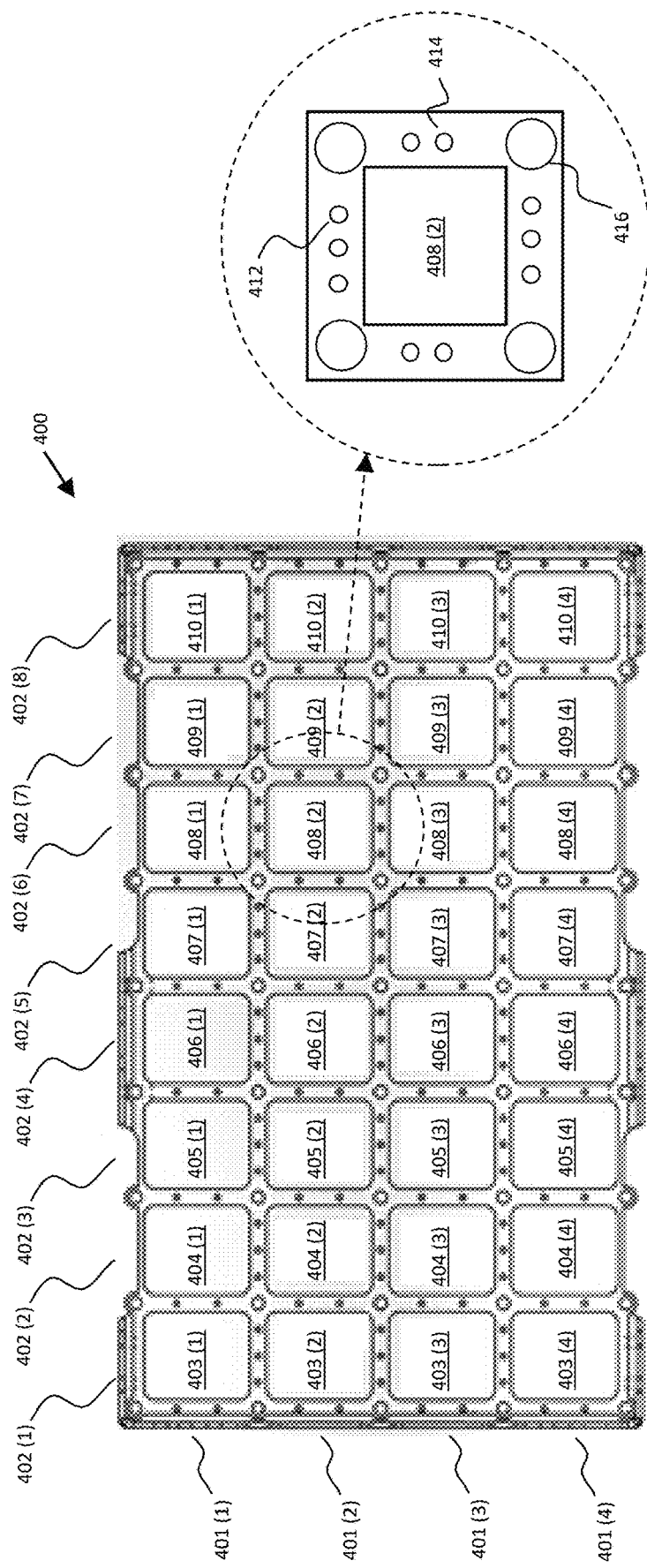
FIG. 4A is a block diagrams depicting the details of the pre-fill tray, according to some embodiments.
FIG. 4B is a detailed view of one of the cells of the block diagram of the pre-fill tray as depicted in 4A, according to some embodiments.

FIGS. 4A and 4B are block diagrams depicting the details of the pre-fill tray, according to some embodiments. FIG. 4A shows a Pre-fill tray 400 is located in the dispensing portion 106 of the robot and below the hopper 301.

FIG. 4A is a block diagram of a top view of a pre-fill tray 400, according to one or more embodiments. Pre-fill tray 400 includes a plurality of chambers or slots that are configured to receive pills from the hopper 301. Chambers or Slots 403(1)-410(4) are arranged in columns 402(1)-402(8) and rows 404(1)-404(4). It is noted that the number of rows and columns are shown for explanatory purposes only, and the actual implementation can have additional, or fewer rows and/or columns, as desired.

The slots 403(1)-410(4) of pre-fill tray 400 are configured to receive several pills of the same or different types. This can be implemented in one of several ways. In some implementations, each slot of the pre-fill tray receives no more than one pill in a pre-fill tray filling operation. However, in other implementations, each slot of the pre-fill tray receives several pills.

In one implementation, the pre-fill tray can have substantially the same dimensions as the blister/pill pack. As a result, each chamber/slot 403(1)-410(4) of the pre-fill tray can hold pills that are dropped to a corresponding element in the pill pack. By using a pre-fill tray 400 that has substantially the same dimensions as a pill pack, transfer of pills is simplified.

In some embodiments, the medications are dispensed by day slots (rows 404) and time slots (columns 402(1)-402(8)) created in the packs according to the information provided by the patient. The time slots are created horizontally to enable the patient to take his or her medication based on the preferred schedule. Of course, the columns and rows may be swapped so that the columns represent days and the rows represent times.

In one embodiment, the slots of the pre-fill tray 400 are square in shape. All the slots in the pre-fill tray are of the same exact dimensions. Alternatively, the slots may be of other shapes and vary in dimensions from other slots in the pre-fill tray 400. Further, the slots may also include movable members that allow each slot to be individually adjusted for size and shape as desired. Other alternatives such as adjusting an entire row or column of slots, or increasing or decreasing the number of slots is alto contemplated.

FIG. 4B is a close up and zoomed in view of one of the chambers or slots of the pre-fill tray 400. Each of the slots of the pre-fill tray 400 includes a plurality of X-directional Pointers 412 and a plurality of Y-directional pointers 414. The X and Y directional pointers allow the robot to read the position of the pre-fill tray 400 with respect to the hopper 301, with respect to another pre-fill tray, or with respect to the pill pack.

In one embodiment, the X-directional pointers are placed between two rows of slots, such as between rows 401(1) and 401(2) or between rows 401(3) and 401(4). In-between each row of slots of the pre-fill tray, there are three X-directional pointers. Likewise, in-between each column of slots, such as between columns 402(1) and 402(2), there are two Y-directional pointers. Other quantities and layouts of pointers are also contemplated.

In another embodiment, each slot of the pre-fill tray 400 includes a door or an open/close mechanism at the bottom of the pre-fill tray. The door, also referred to as tray door, covers the slots of the pre-fill tray such that pills that are deposited in the pre-fill tray are held inside the slots if the trap door is in a closed position. The door may be configured such that the bottom of all the slots opens at the same time. Alternatively, there may be separate doors for each slot or separate doors for each row or column allowing opening and closing of each slot door or each row door as desired. When the door is in an open position, the pills in the slots controlled by the door are dropped into the receptacle below (such as another pre-fill tray or a pill pack).

Figure 4C:
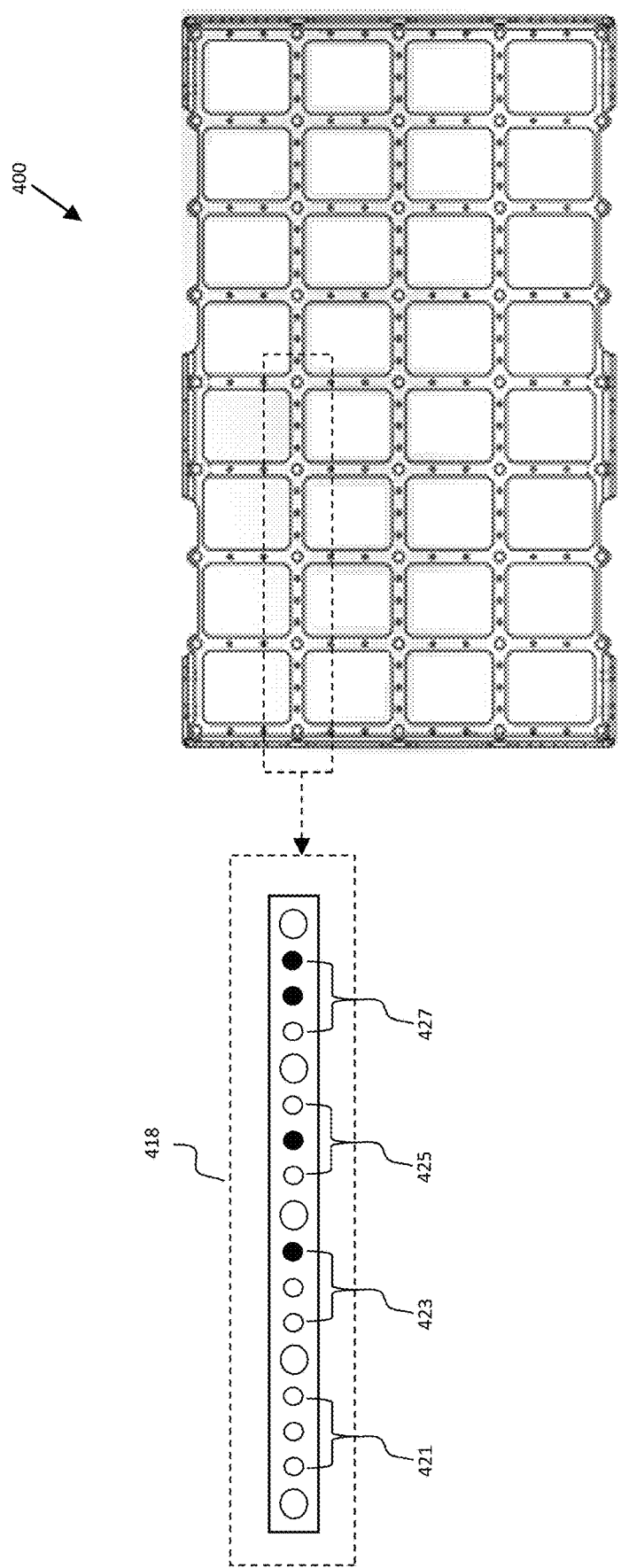
FIG. 4C is a detailed view of a portion of the common wall in-between two rows of cell of the pre-fill tray, according to some embodiments.

FIG. 4C is a close up and zoomed in view of the X-directional pointers in the pre-fill tray 400. As shown in FIG. 4C, for each slot, there are three X-directional pointers in-between two rows of slots. In one embodiment, the X-directional pointers are holes that are either open or holes that have been filled and closed. For example, a small cross-section of the x-directional pointers is shown at 418. Each set of three X-directional pointers are populated strategically such that a sensor reading these slots would immediately recognize the current X-directional position, i.e. the X-directional coordinates, of the particular slot that correspond to the X-directional pointer. In this example, the configuration of the x-directional pointers, i.e. the holes, in the cross section 418 is populated as open, open, open 421, followed by open, open, closed 423, followed by open, closed, open 425, and closed, closed, open 427.

Referring back to FIG. 4B, similar to the methodology used for X-directional pointers, Y-directional pointers are used as well. In one embodiment, there are two, Y-directional pointers placed in the column between two columns of slots.

Each of the slots of the pre-fill tray 400 also includes a corner pointer 416. The corner pointers provide alignment guidance to the hopper's corner sensors such that the four corner sensors of the hopper are properly overlaid and aligned with the four corner pointers of the pre-fill tray.

The X and Y directional pointers, along with the corner pointers, are read by various sensors in the robot 100 to accurately locate the X and Y coordinate of both the Pre-fill tray 400 as well as each chamber/slot of the pre-fill tray. Further, the coordinates are used for calculating the distance from each slot of the pre-fill tray to its desired position and thereby to displace the pre-fill tray in the desired direction.

The X and Y directional pointers, along with the corner pointers, are read by various sensors in the robot 100 to accurately locate the X and Y coordinate of both the Pre-fill tray 400 as well as each chamber/slot of the pre-fill tray. Further, the coordinates are used for calculating the distance from each slot of the pre-fill tray to its desired position and thereby to displace the pre-fill tray in the desired direction.

In one embodiment, the pre-fill tray 400 includes eight X-directional pointers and four Y-directional pointers. The X-directional pointers allow for a possible 0 to 7 locations to be read by the system. They are represented using a 3-bit binary numbering scheme, such 000, 001, 010, 011, 100, 101, 110, and 111. In one configuration, a "0" is associated with an "open" and a "1" is associated with a closed position. Using this methodology, a slot with X-directional pointer that has a 000 is associated with open, open, open reading whereas a X-directional pointer with 101 is associated with a closed, open, closed reading.

Likewise, a Y-directional pointer with a 00 is associated with a open, open reading, while a Y-directional pointer with 10 is associated with a closed, open reading.

Further, there are 4 corners pointers for each slot, so 4 holes and when they align with the sensors pointed in FIG. 3B 317, 319, 321, 323 the sensors read value 0, which means the slot is completely, properly aligned with the small hopper. This represents a state called "Slot Positioned" which is used in the software or algorithm to start the slot number verification process.

Figure 5B:
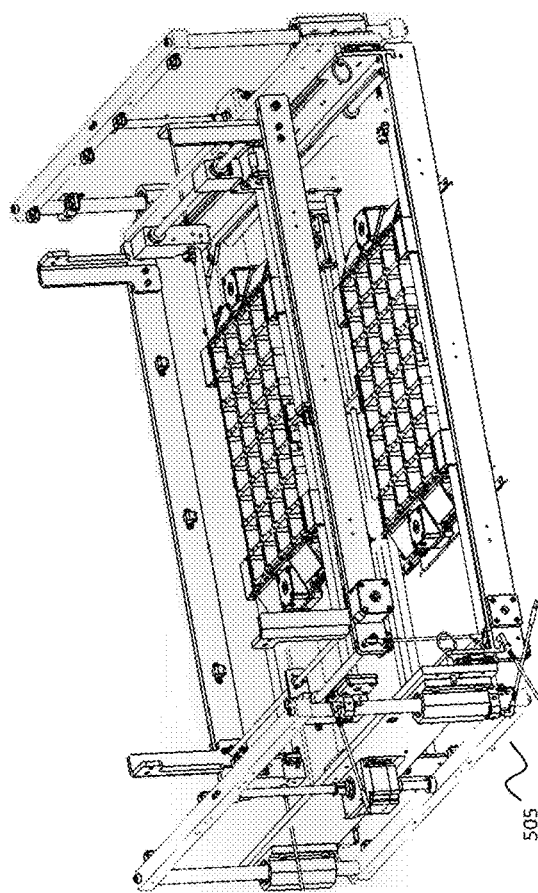
FIG. 5B depicts the arrangement of a plurality of the pre-fill trays located inside the machine body of the robot, according to some embodiments.
Figure 5A:
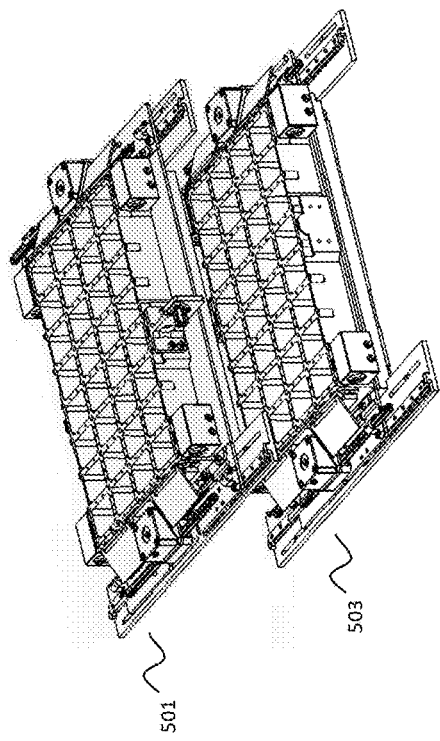
FIG. 5A depicts the arrangement of the top and bottom pre-fill, according to some embodiments.

FIGS. 5A and 5B depict the arrangement of a plurality of the pre-fill trays located inside the machine body of the robot, according to some embodiments. As shown in FIG. 5A, in one embodiment, the robot 100 includes a top pre-fill tray 501 and a bottom pre-fill tray 503. Both pre-fill trays are exactly of same size and dimensions. Further, the slots of the top pre-fill tray 501 match the slots of the bottom pre-fill tray 503. This allows the pills located in the slots of the top pre-fill tray 503 to be dropped into slots in the bottom pre-fill tray 503 such that the bottom pre-fill tray replicates the exact same pills in the same slot configurations as the above pre-fill tray 501. FIG. 5B depicts the location and positioning of both pre-fill trays in the machine body of the robot.

The top pre-fill tray 501 and the bottom pre-fill tray 503 are capable of moving independent from one another in an X or Y direction within the allowable distances in the machine body. The robot may control the movements of both top pre-fill tray 501 and the bottom pre-fill tray 503. For example, in one instance, when pills are needed to be dropped from top pre-fill tray 501 to bottom pre-fill tray 503, the robot would displace either one, or both pre-fill trays until they are perfectly aligned in the X-Y direction such that a drop from the top pre-fill tray 501 is accurately deposited in the bottom pre-fill tray 503 without any pills spilling over outside the slots.

Likewise, in another instance, when pills are needed to be dropped from bottom pre-fill tray 501 to a pill pack located beneath the bottom pre-fill tray 503, the robot may displace the bottom pre-fill tray 503 until it is aligned with the pill pack below.

Further, in yet another instance, when pills are to be received by the top pre-fill tray 501 from the hopper 400, the robot may determine the location of the slot in the top pre-fill tray in which the pills are to be dropped, and then displace the top pre-fill tray 501 until the desired slot aligns with the hopper 301. In this example, when the robot 100 desires for the top pre-fill tray 501 to be aligned with the hopper 301, the robot ensures that the four corner sensors 317, 319, 321, and 323 in the hopper 301 are aligned with the corner pointers 416 in the top pre-fill tray 501. When aligned is confirmed, the robot signals the hopper to drop the pills from the hopper 310 into the top pre-fill tray 501.

Among several advantages, the top and bottom pre-fill tray feedback system, allows for a high efficiency dispensing system. The queuing capability provided through the top and bottom pre-fill tray system allows dispensing of pills from the Canisters and manual pre-fill trays without having to stop dispensing until completion of one pill pack. This configuration allows dispensing of multiple pill packs at a time while at the same time ensuring that the pills designated for the desired pill pack are not mixed with that of another pill pack, i.e., the system is capable of either dispensing pills for multiple patients at a time or pill for the same patient that may have to be packaged in separate pill packs.

In operation, once a set of pills are dispensed that are designated for a first pill pack, and clear a section of the system, then a second set of pills designated for a second pill packs can be dispensed. Since the hopper system and the plurality of pre-fil trays include mechanisms, such as trap doors, they allow for separation of compartments within the dispensing system thereby allowing parallel processing of multiple pill packs at a time resulting in a high efficiency system. Although a first and second pill pack are described in this paragraph, the system is not so limited and is capable of parallel processing multiple pills at a time.

Figure 6:
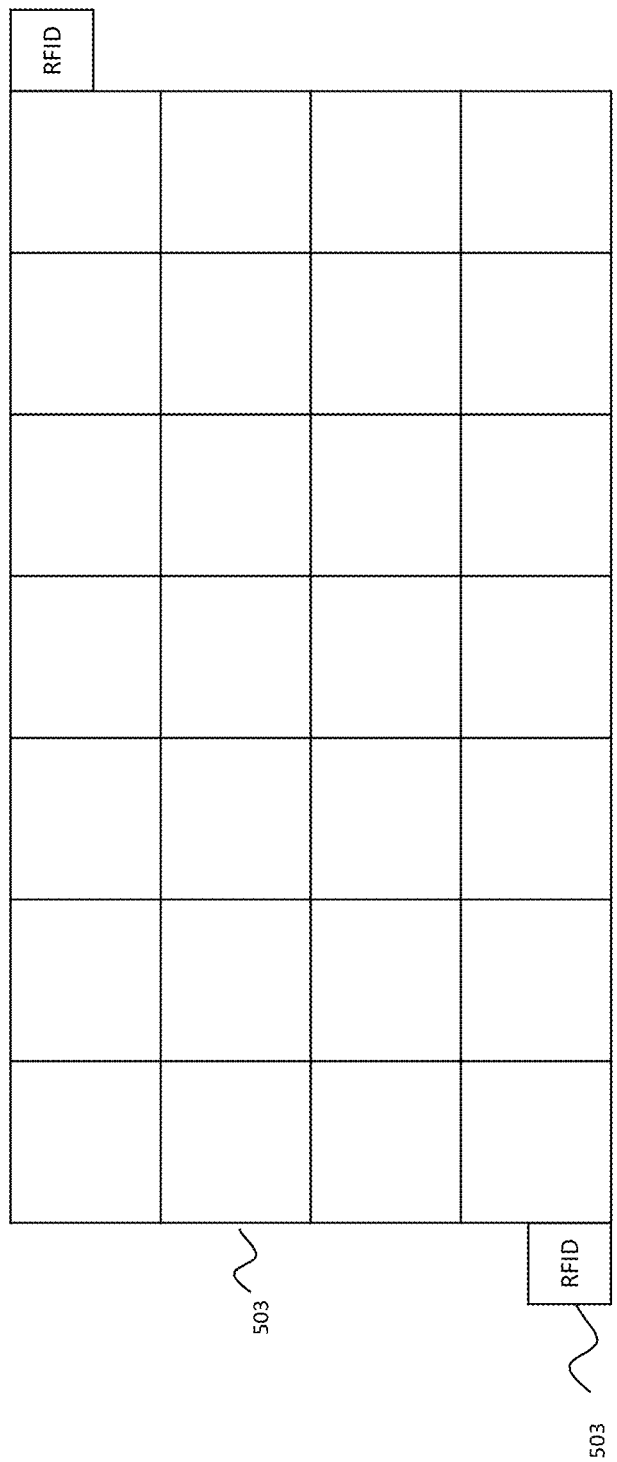
FIG. 6 is a block diagram of the lower pre-fill tray with an RFID tag, according to some embodiments.

FIG. 6 is a block diagram of the lower pre-fill tray with an RFID tag, according to some embodiments. The lower pre-fill tray 503 includes a plurality of radio frequency identification (RFID) tags. The RFID tags contain electronically stored information that is transmitted to them from the robot 100. The RFID tag relates to a different drug or medicine or prescription plan associate with a patient. The robot 100 uses RFID tags of the bottom pre-fill tray 503 and determines if there is a match with the empty pill pack located beneath the lower pre-fill tray 503. Once a match is confirmed, i.e. a determination has been made that the pills in the lower pre-fill tray 503 matches the prescription that was prescribed for the patient and according to the plan, and that the pill pack located beneath has been identified as the pill pack for that specific patient, then robot 100 allows the pills to drop from the lower pre-fill tray 503 into the desired pill pack. The RFID checking ensures that only the medicines designated for the patient is populated in the correct pill pack.

Figure 7B:
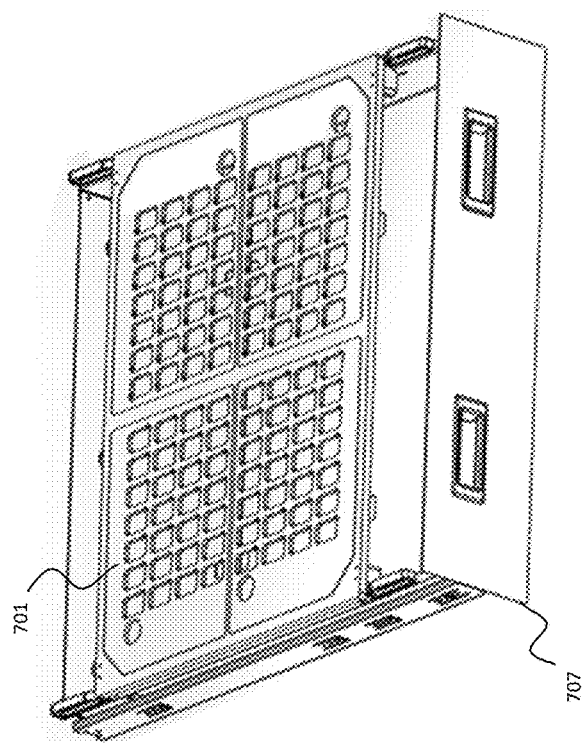
FIG. 7B depicts an isometric view of the packing plate (pack plate), according to some embodiments.
Figure 7A:
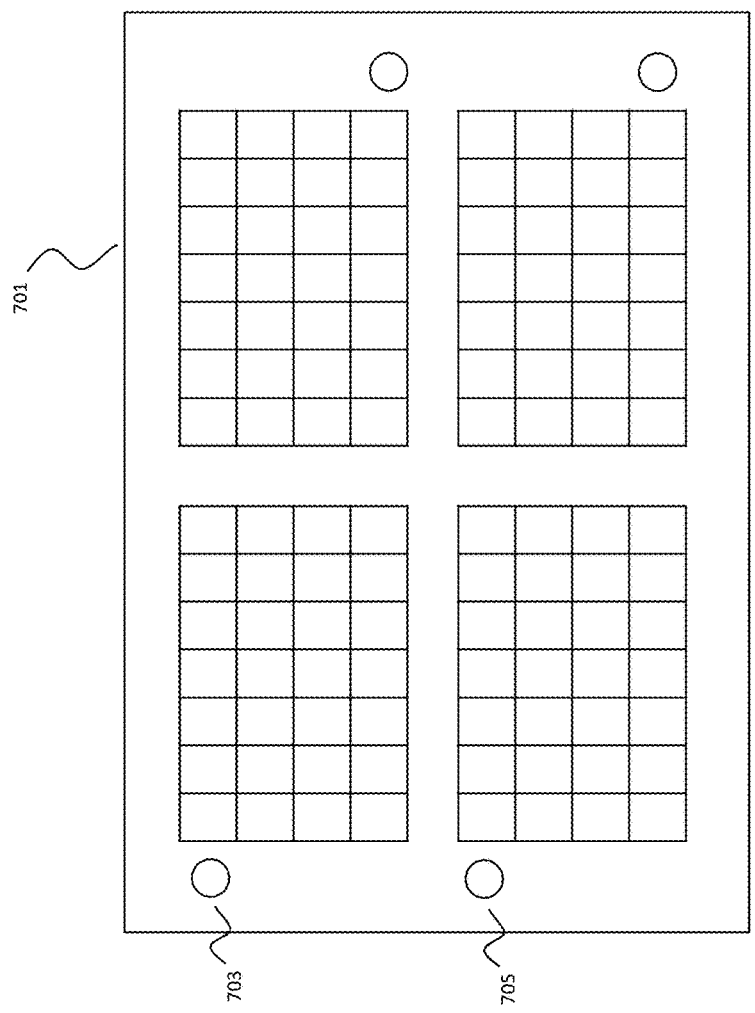
FIG. 7A depicts the top view of the packing plate (pack plate), according to some embodiments.
Figure 8:
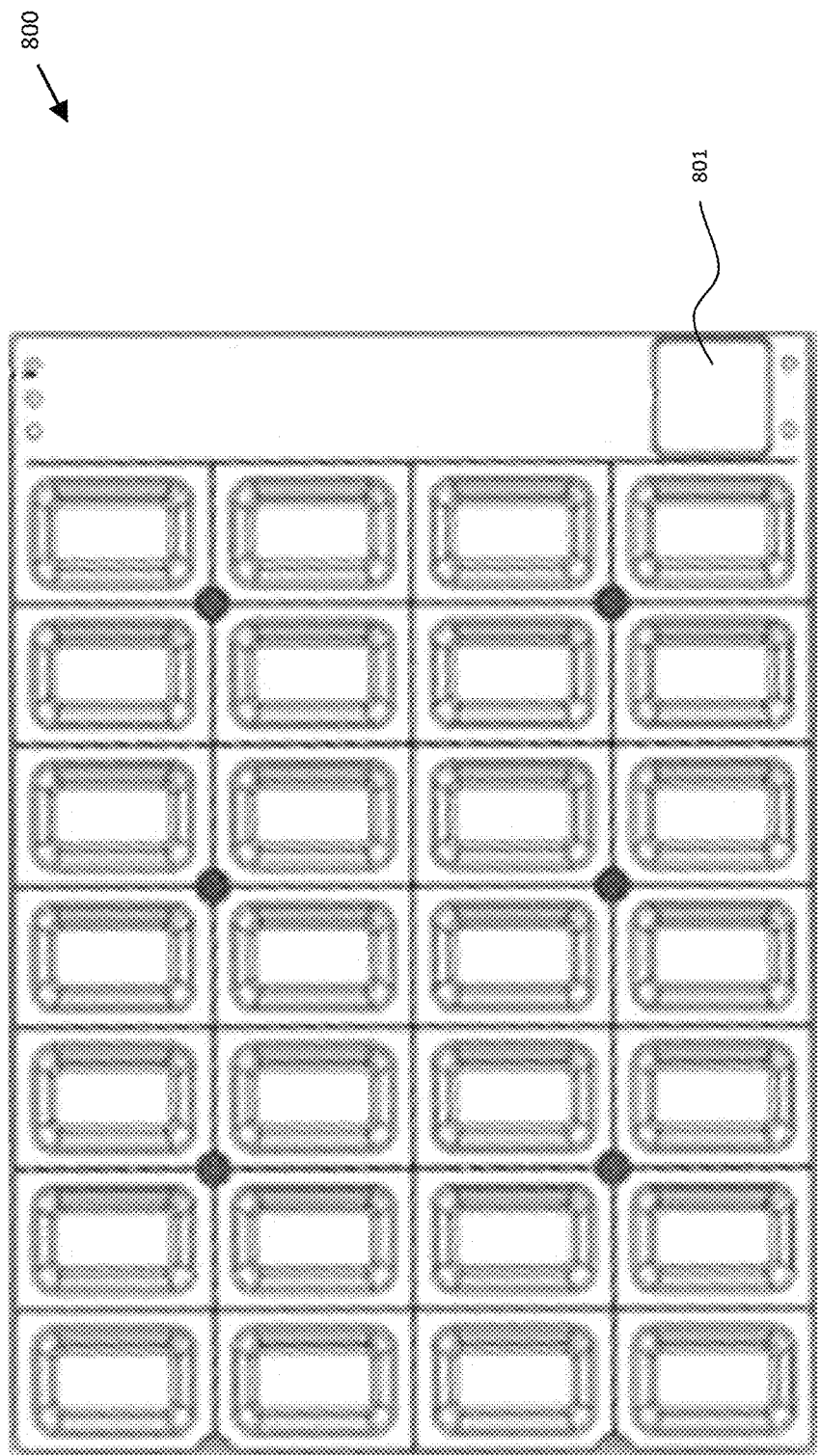
FIG. 8 is a top view of a pill pack (or blister Pack) used by the pill dispensing robot, according to some embodiments.

FIGS. 7A and 7B depict the packing plate (pack plate), according to some embodiments. The packing plate 701, also referred to as pack plate, is a structure that has a plurality of slots to accept a pill or blister pack. Each slot in the pack plate is designed to accept a pill pack. The slot of the pack plate allows for a snug fit of the pill pack such that once the pill pack is inserted in the slot, it cannot move in any X or Y direction and also cannot move with respect to the packing plate The pack plate 701 is designed to accept a plurality of pill/blister packs. As shown in FIG. 8, a blister pack 800 is essentially the final pill pack 800 that is used by a patient and includes the pills designated for the patient in accordance with the prescription plan. In one embodiment, the packing plate 701 includes four slots that allow insertion of four pill packs at a time into the packing plate. Other configurations, shapes, and numbers of slots are also contemplated.

The pill pack can have a four by seven (or another, such as 4 by 8) slot arrangement. The pill pack can contains patient name, a picture, and a large amount of information about the contained pills, such as when to take them, and any concerns/side effects with each drug.

The packing plate also includes radio frequency identification (RFID) tags 703 and 705. These packing plate RFID tags are used to ensure that a desired pill pack 800 is placed in the desired location of the packing plate.

Since the bottom pre-fill tray 503 holds medicines for one pill pack at a time, in operation, the robot determines the correct pill pack and its position, and then displaces the bottom pre-fill tray 503 such that the bottom pre-fill tray aligns directly on top of the desired pill pack and then drops the medicines into it. It should be notes that the configuration and the dimensions of the slots in the bottom pre-fill tray match those of the pill pack 800 such that the pills are dropped accurately into each slot of the pill pack as desired and there is no spill over into any other slots of the pill pack.

Although certain four pill packs are shown, the invention is not so limited and other numbers of pills packs, various configurations, shapes and orientations are also contemplated.

As mentioned above, FIG. 8 is a block diagram of a pill pack (or blister Pack) used by the pill dispensing robot, according to some embodiments. The pill pack 800 also includes an RFID tag 801. The RFID tag contains patient information, such as patient name, birth date, types of prescriptions and pills designated for the patient and other patient data relevant and needed by the pharmacies or the system to operate. The robot 100 checks and verifies the RFID tag 801 on the pill pack prior to populating it with the pills from the pre-fill trays. The RFID assurance check ensures that the correct pills that are designated for the right patient are being deposited in the correct pill pack that is designated for the patient. Quality assurance and verification through such RFID check minimizes and error and accidental mishaps, such as a wrong medication being provided to the wrong patient or deposition of a morning medicine accidentally in the evening slot.

FIG. 9 is a flowchart illustrating one method of operation of the pill dispensing robot, according to some embodiments. It is noted that the flowchart 900 can be performed by one or more modules that access robot 100. As will be appreciated in light of the present disclosure, this method may be modified in order to derive alternative embodiments. Also, the steps in this embodiment are shown in sequential order. However, certain steps may occur in a different order than shown, certain steps may be performed concurrently, certain steps may be combined with other steps, and certain steps may be absent in another embodiment. Method 900 is described with reference to variations of the elements described in connection with FIG. 1.

At 901, a plan generation module accesses a prescription plan, where the plan indicates a first pill distribution for a first time period, and a second pill distribution for a second time period. For example, the first pill distribution for a first time period may relate to a specific patient taking a medication named Tylenol 500 mg at 9 AM in the morning and the second pill distribution for a second time period may relate to the same patient taking a medication named Metoporlol at 12 Noon.

The plan accessed by the prescription plan generation module can be a new plan, in which case the plan generation module generates a new plan. The plan can be an existing plan, in which case the plan generation module modifies the existing plan (or generates another plan based on the existing plan). The plan generation module can receive input (such as user input) that modifies the existing plan.

The goal of the plan is to dispense pills for a specific patient that are in accordance to the medication prescribed by their doctor or caregiver and package such medication into a pill pack, such as the pill pack shown in FIG. 8. The pill pack is typically organized by hours of administration (HOA) that includes, for example, the amount of a first drug that is to be administered to a patient in a morning time slot, the amount of a second drug that is to be administered to the patient in the same time slot. The pill pack also includes similar pills that are distributed and labeled for use during other time slots. The plan generation module is configured to receive input from a user that modifies the distribution, type, and number of pills as indicated by the plan.

The plan can be provided using a network, memory (if both the plan generation module and the control module are implemented using the same computing device), using some memory medium (e.g., a tangible memory storage medium), or using another technique. The plan may also be provided over Wifi, attachment of an external device, such as USB drive, or through other means.

At 901, the robot 100 performs the functionality as indicated by the prescription plan. In that, the robot 100 selects one or more pills, according to the plan, from one or more of the canisters 110, located in the canister drawers 108, or the manual fill trays that are in the manual fill tray section 104. The pills selected from either the canisters or the manual fill trays are then dropped into the dispensing section 106 (Reference to FIG. 1).

At 903, the pills dispensed from the canisters 110 and manual fill trays are dropped into the hopper system 207 (referring to FIG. 2). As mentioned above, the hopper system is located in the dispensing section 106. Once the selected pills are dropped from the canisters 110 and manual fill trays, the pills make their way through the hopper 207, entering through the wider top of the hopper and exiting through the narrower bottom of the hopper 207.

In an alternate embodiment, the above configuration also may include a small hopper (not shown). The small hopper may be placed underneath the hopper 207, which may also be referred to as the bigger hopper. The small hopper may include a wider top and a narrower bottom and include a tunnel at its bottom exit section. The tunnel has a certain height that prevents medicines from bouncing back into the small hopper when they are dropped. The tunnel also includes a tunnel wall that prevents medicines from slipping into another slot of the top pre-fill tray 209. The tunnel opening should be smaller than the slots in the pre-fill tray 209, so the tunnel wall covers the top of a slot opening to prevent medicines from falling or bouncing out.

At 905, the pills from the hopper 207, or alternatively from the small hopper, are dropped into the top pre-fill tray 209. This step requires the hopper 207 to align with the slots of the top pre-fill tray 209. Since the hopper 207 holds pills on a slot by slot basis, i.e. for each specific slot at a time, the drop process requires the hopper 207 to be aligned with the particular slot in the pre-fill tray 209 that is associated with the pills. For example, if the pills are for a Tuesday and to be take in the afternoon, the top pre-fill tray 207 would have a specific slot for such day and time and the hopper 207 would need to align with that particular slot. It should be noted that the slots of the top and bottom pre-fill tray match the day and time slots in the final pill pack. The alignment process to align the intended slot in the pre-fill tray 207 and the hopper is described in more detail in FIG. 11 below.

At 907, the pills collected in the slots of the top pre-fill tray 207 are released and dropped into the bottom pre-fill tray 211. The release may be through a tray door located at the bottom of the top pre-fill tray 209 that is controlled by the robot 100. The release may be performed when the timing is right for the drop and not before or after. For example, the release may occur only after the top pre-fill tray 207 and the bottom pre-fill tray are aligned to ensure an accurate drop that mirrors the configurations of the pills in the top pre-fill tray 207 to that of the bottom pre-fill tray 209, i.e. essentially, the bottom pre-fill tray 209 would hold the pills in the exact same slots, in the same configuration, as the top pre-fill tray. The alignment process to align the top pre-fill tray 207 with the bottom pre-fill tray 209 is described in more detail in FIG. 13 below.

At 909, certain verifications are performed by the robot 100 in order to accurately process the medications and package them into a pill pack. In one embodiment, the packing plate 213 holds four separate pill packs. One of the verifications performed would be to identify the correct pill pack from among the four pill packs placed in the packing plate 213. Another verification would be to match the patient data with the pills held in the pre-fill trays prior to dropping them into the pill pack. These verifications may be performed by using an RFID tag that is located on the pill pack that contains all the patient data. One exemplary operation of this verification is mentioned next.

In one embodiment, the pill pack is verified to ensure that the pills are dispensed in a pill pack that is designated for the specific patient. As mentioned above, the packing plate 701 include a plurality of RFID readers. The packing plate 701 also includes four slots that can allow a potential of four pill packs to be placed in them, such that there is one pill pack in each slot.

Once a pill pack 800 is placed in a slot, the system detects its placement. The system is capable of detecting both when a pill pack is placed in any of the slots as well as when a pill pack is removed from any of the slots.

The pill pack also includes an RFID tag. This pill pack RFID tag holds patient information that is associated with only one specific patient. When a new pack is placed in any of the slots of the packing plate, the system detects the pill pack and reads the value of the pill pack RFID tag. At this point, the system queries for the associated pill pack information to determine whether it's a new pill pack or an old pill pack. If the database query returns "no previous packs associated" then it means this pack is a new pack thereby verifying that this specific prescription has not been filled for this specific patient in the past. Once the verification is successful, the pills from the bottom pre-fill tray are dropped into the pill pack.

On the other hand, if the database query returns a pack-id associated with the RFID, this signifies that the pill pack may have been previously used or is associated with another patient. These results in an unsuccessful verification thereby stopping the operation such that the pills that have been held in the bottom pre-fill tray are not dispensed into this pack, i.e., the wrong pack that is not associated with the pills. Such verification matches pills with patient data and provides yet another verification and accuracy check.

At 911, once the verification result in a positive outcome, for example the patient name and data match with the pills prescribed for the patient and held in the pre-fill trays, then the pills are dropped into the appropriate pill pack.

Figure 10A:
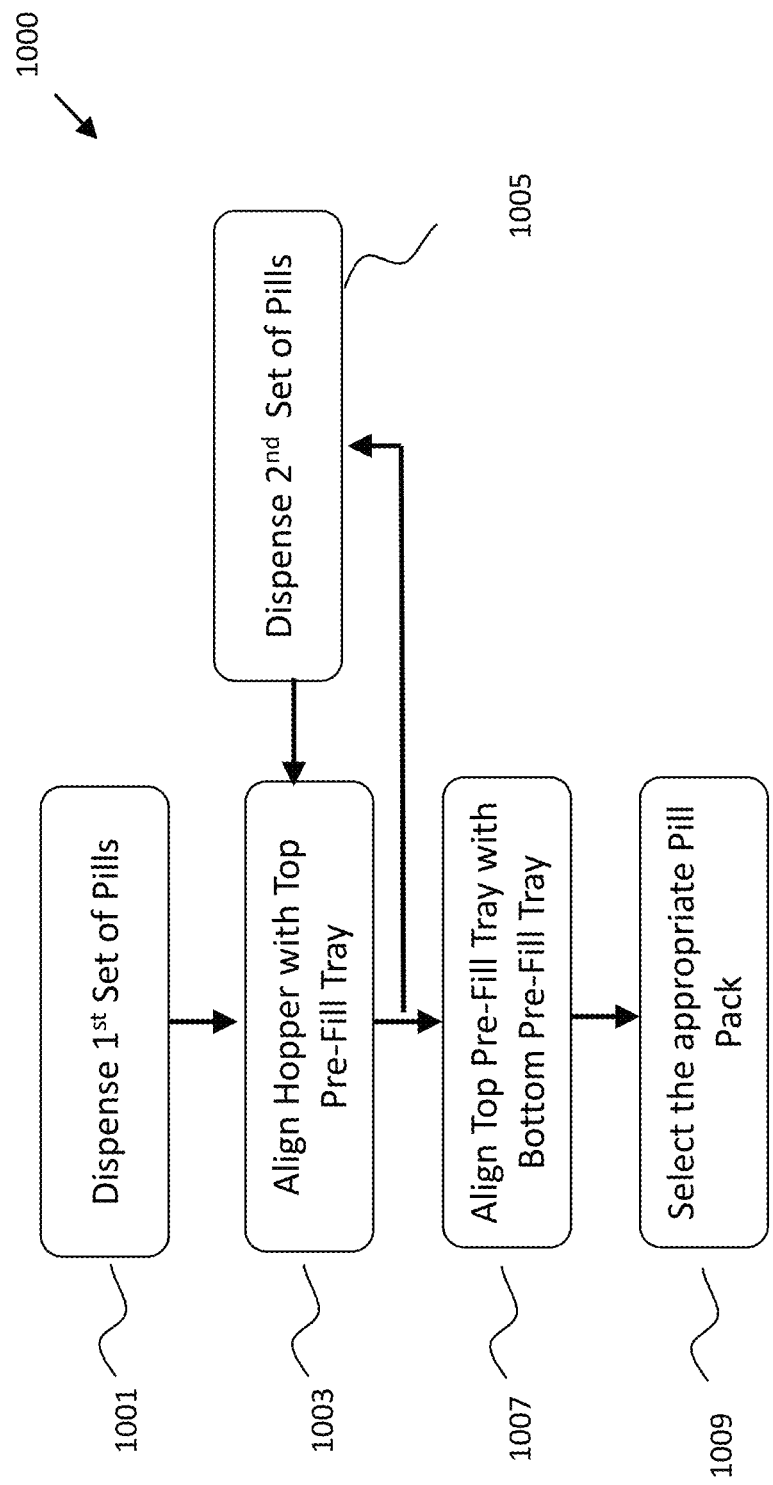
FIG. 10A is a flowchart illustrating the alignment operations performed in the robot 100, according to some embodiments.
Figure 10B:
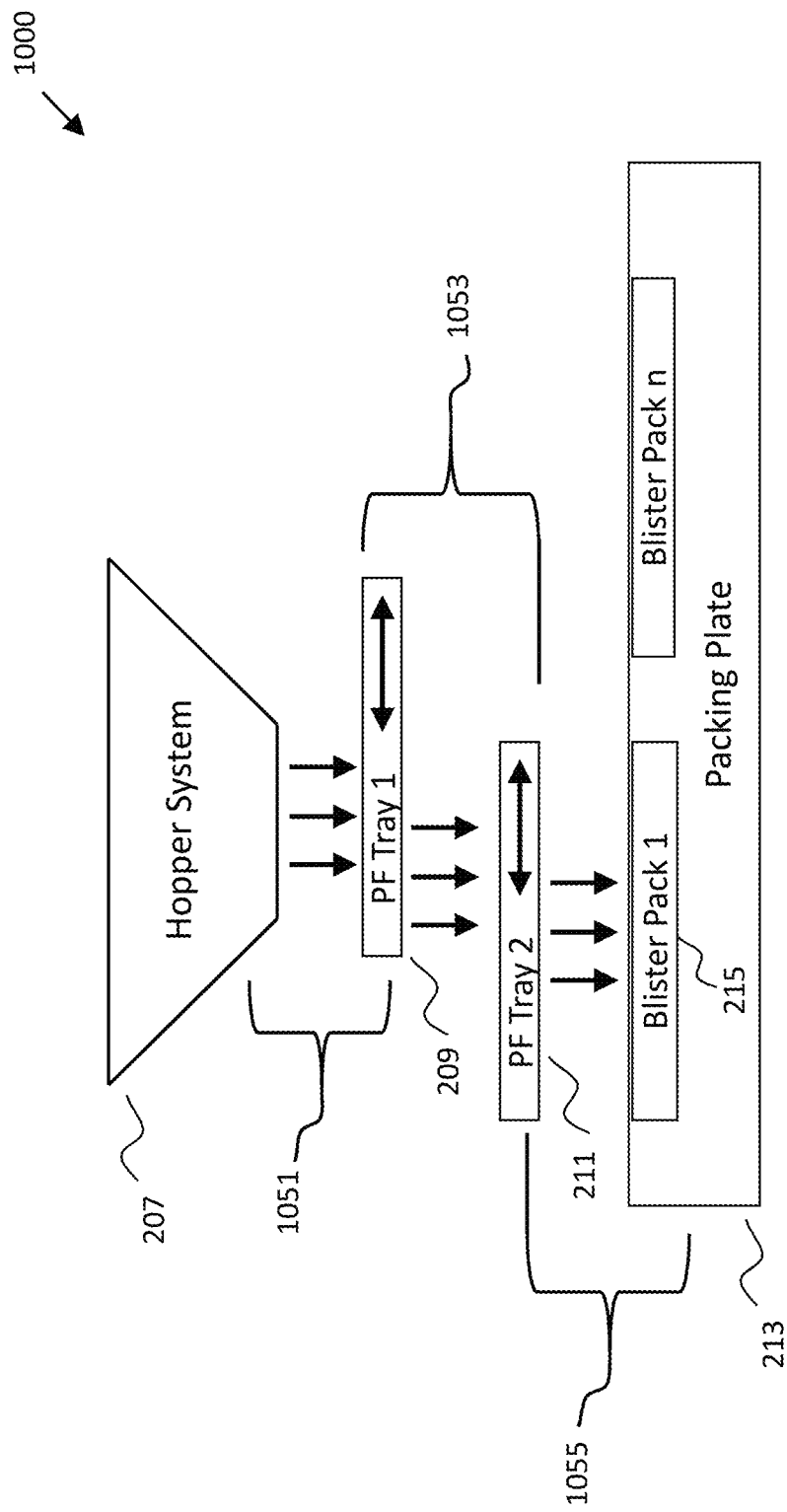
FIG. 10B is a block diagram illustrating some of the components of the robot that are used during the alignment operations, according to some embodiments.

FIG. 10A is a flowchart illustrating the alignment operations 1000 performed in the robot 100, according to some embodiments. FIG. 10B is a block diagram illustrating the three alignments that are part of the operation explained in FIG. 10A.

FIGS. 10A and 10B will be used to explain the alignment processes that are performed by the robot 100. In one embodiment, the robot performs three separate alignment processes. The alignment processes include, alignment process 1051, the alignment of hopper 207 with the top pre-fill tray 209, alignment process 1053, the alignment of top pre-fill tray 209 with the bottom pre-fill tray 211, and alignment process 1055, the alignment of the bottom pre-fill tray 211 with the intended pill/blister pack 215 that is located in the packing plate 213.

Referring to FIG. 10A, at 1001, pills are dispensed into the hopper 207. At 1003 the hopper 207 is aligned with the top pre-fill tray 209. More specifically, the hopper 207 is aligned with the intended chamber/slot in the top pre-fill tray 209 in which the medications held by the hopper are to be deposited.

Figure 11:
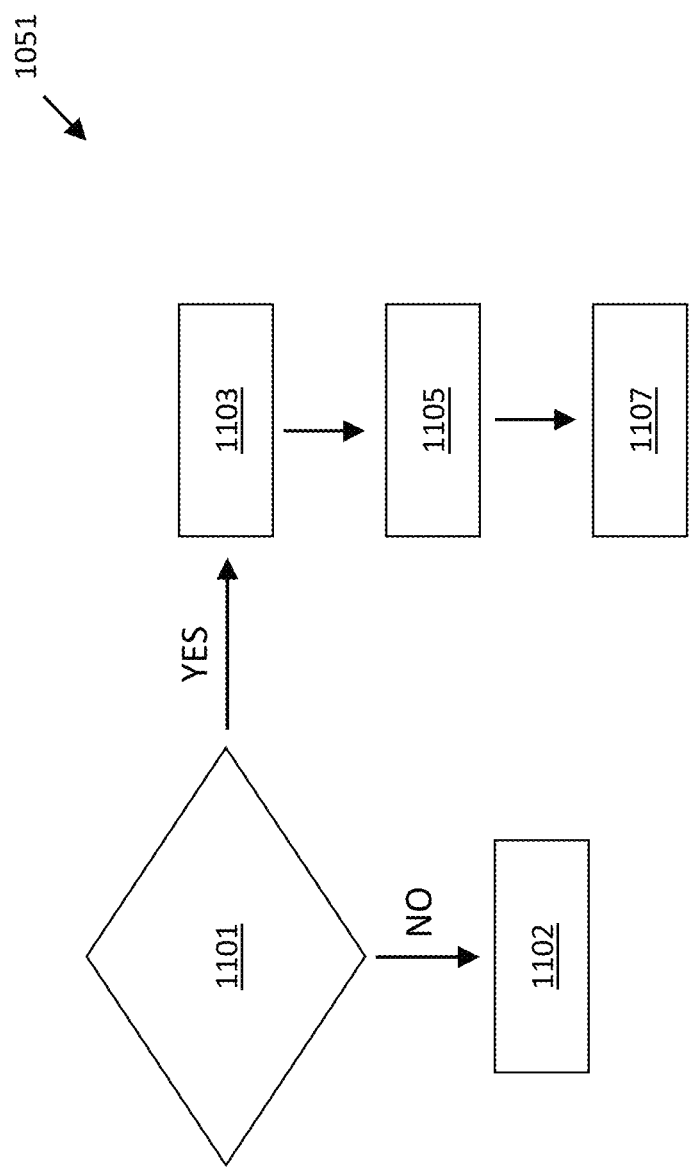
FIG. 11 is a flowchart of a method of aligning the hopper with the top pre-fill tray, according to some embodiments.

FIG. 11 is a flowchart of a method of aligning the hopper with the top pre-fill tray, according to some embodiments. At 1101, with reference to FIGS. 3A, 3B, 4A, 4B, and 4C, the corner sensors 317, 319, 321, and 323, of the hopper 301 are used to detect the four corner pointers 416 of the top pre-fill tray 209. Alignment of all the four corner sensors of the hopper 207 with the four pointers of the top pre-fill tray confirms that the exit of the hopper 207 is directly above one of the slots of the pre-fill tray 209.

At 1102, if the corner sensors of the hopper 207 and the corner pointers of the top pre-fill tray 207 are misaligned, or unable to align, or unable to be read, then a fatal error is indicated and another attempt is made to align the four sensors with the nearest four slot pointers.

At 1103, once the four corner sensors in the hopper match up with the four corner pointers of a certain slot in the top pre-fill tray below, the X-directional sensors 305, 307, 309, and 311 in the hopper 207 are used for reading X-directional pointers 412 in the top pre-fill tray 209 and thereby determine the X Coordinates of the certain slot in the top pre-fill tray 209 that is directly underneath the hopper 207.

Likewise, at 1105 once the four corner sensors of hopper 207 match up with the four corner pointers in the top pre-fill tray, the Y-directional sensors 313 and 315 in the hopper 207 are used for reading the Y-directional pointers 414 in the top pre-fill tray 209 thereby determining the Y-coordinates of the certain slot in the top pre-fill tray 209 that is directly underneath the hopper 207.

At 1107, after obtaining the X & Y coordinates of the slot that is directly underneath the hopper 207, the robot sends a signal to the top pre-fill tray 209 to move in a certain direction so that the desired slot in the pre-fill tray 209 is brought directly underneath the hopper 207.

Figure 12:
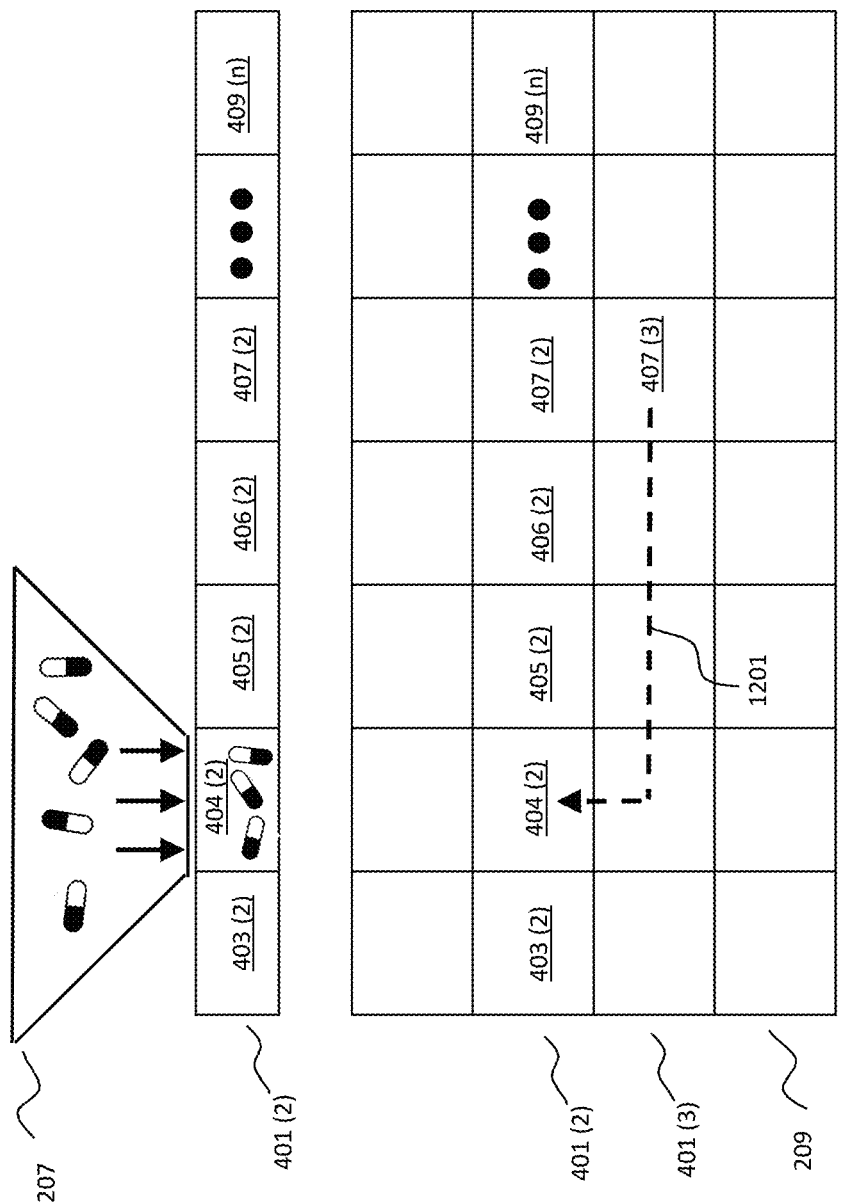
FIG. 12 is a block diagram illustrating the dropping of the pills from the hopper to a desired slot in the top pre-fill tray, according to some embodiments.

FIG. 12 is a block diagram illustrating the dropping of the pills from the hopper 207 to one of the desired slots in the top pre-fill tray, according to some embodiments. In one example, if the current slot underneath the hopper is in row 401(3) and is slot number 407(3), and the desired slot in which the pills are to be dropped is in row 401(2) and slot number 404(2), then the robot having aligned the corner sensors, the corner pointers, and X & Y sensors and X&Y pointers will be aware of the coordinates of the slot that is underneath the hopper. Based on calculations, as shown by the path 1201, the robot 100 may signal the top pre-fill tray to move left a certain distance, thereby moving in X direction to for the length of about three columns, and then a shorter Y distance, to move the length of about one row in the Y direction. Other alternative paths may also be followed and techniques such as to determine shortest or fastest route may also be followed.

At shown in FIG. 12, after the alignment is confirmed and the desired slot 404(2) is underneath the hopper 207, then the pills from the hopper 207 would be dropped into slot number 404(2). Likewise, the robot may use the slot 404(2) as the initial position, make all the X and Y directional calculations and then signal the top pre-fill tray 209 to move after slot 404 (2) has been filled to the next desired slot. In this manner, each slot of the top pre-fill tray 209 is positioned one by one underneath the hopper 207 and all the slots in the top pre-fill tray 209 are filled with pills. It should be noted that partial fills of the top pre-fill tray or some combinations of pill drops are also contemplated.

Referring back to FIG. 10A, at 1005, a $2^{nd}$ set of pills are dispensed into the hopper 207. In operation, as soon as the hopper drops the $1^{st}$ set of pills into the top pre-fill tray 209, the hopper is empty and available again to receive a $2^{nd}$ set of pills. The pre-fill trays add a buffer and a time delay such that parallel processing can be done with constantly dropping pills for one slot in the pre-fill tray after another to produce a efficient, fast processing system that doesn't have to wait for the pills to go all the way through the robot 100 to then drop the next set.

Step 1005, the separating the pills from the hopper 207 to the top pre-fill tray by emptying the hopper and then filling it up again for the $2^{nd}$ set of pills, allows the separated pills to be collected and stored in the top-pre-fill tray 209 and then make their way into the bottom pre-fill tray 211; while independently, the pill pack can be selected and maneuvered into its place. This separation of processes implements a buffer, that allows the pills to be selected and dropped into the pre-fill tray, without needing to line up the pill pack for each element, and without needing to wait for each such element to be filled (i.e., as each pill selection is dropped into a corresponding pill element of the pill pack). Once the pill pack is lined up (e.g., underneath the transfer plate), the pills are dropped from the bottom pre-fill tray onto the pill pack.

Referring back to FIG. 10A, at 1007, the alignment process 1053 aligns the top pre-fill tray 209 with the bottom pre-fill tray 211. The alignment process 1053 is explained in details in FIG. 13 below.

Figure 13:
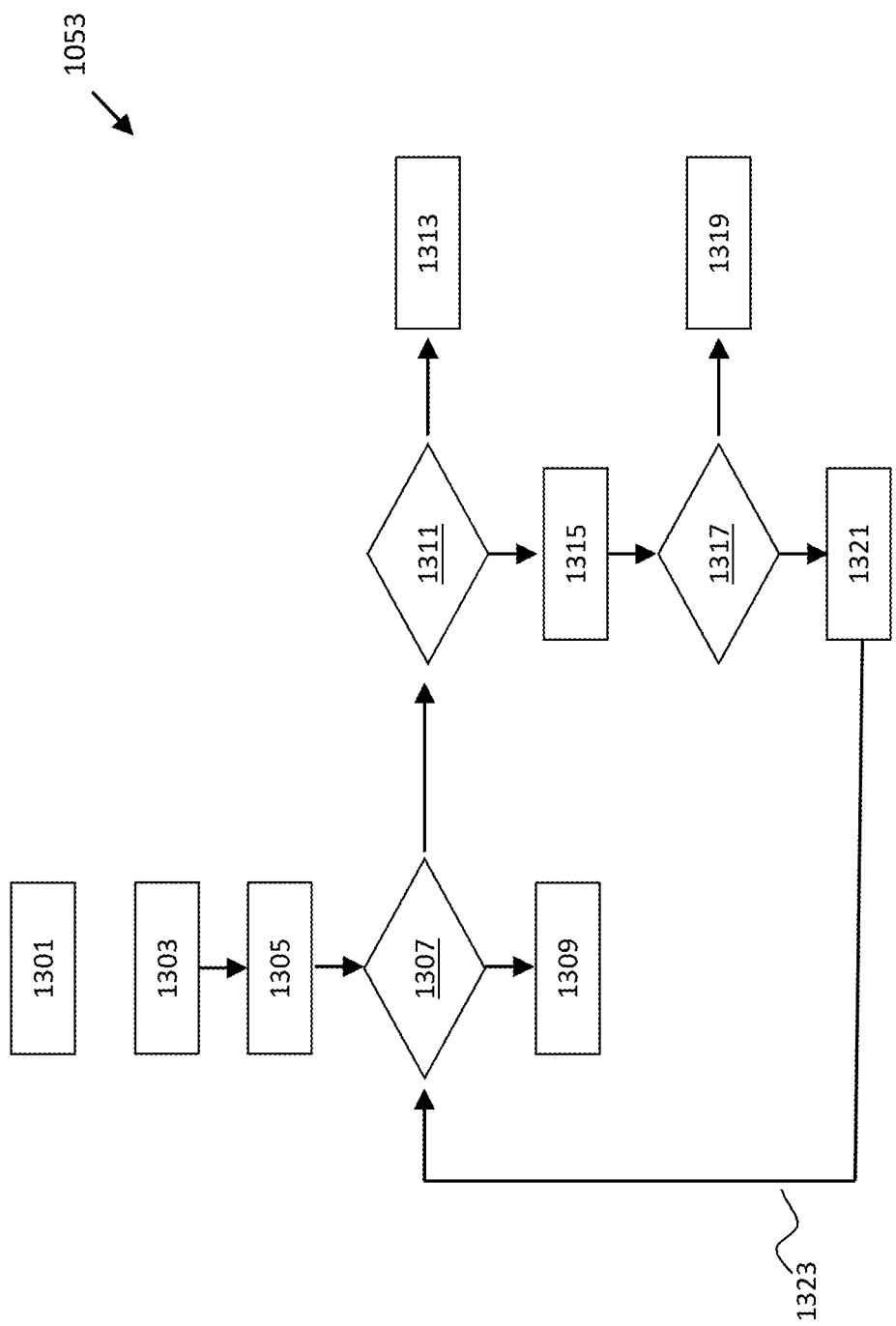
FIG. 13 is a flowchart of a method of aligning the top pre-fill tray with the bottom pre-fill tray, according to some embodiments.

FIG. 13 is a flowchart of a method of aligning the top pre-fill tray 209 with the bottom pre-fill tray 211, according to some embodiments.

At 1301, the robot 100 commands the top pre-fill tray 209 to a reset to get to an initial X and Y coordinate position of (0, 0).

At 1303, the robot 100 sets a try count from zero to maximum integer. This maximum integer is the number of times the pre-fill tray will try and move in order to get to its final destination. For example, if the pre-fill tray's maximum count is set to three, then after three failed attempts to get to its final destination, an error code will be displayed and the alignment process stopped. The try count is essentially the number of tries the pre-fill tray will undergo.

At 1305, robot 100 reads the current position of the top pre-fill tray 209.

At 1307, robot 100 determines the try count and if it is less than the maximum then it will proceed forward with the alignment process. If the try count has already been reached, then at 1309 a fatal error message is displayed.

At 1311, the robot 100 determines the current position of the top pre-fill tray 209. If the current position of the top pre-fill tray is where the pre-fill tray needs to be, i.e., it desired position, then at 1313 no movement is needed and the process is completed. In essence, this indicates that the top pre-fill tray 209 is aligned already with the bottom pre-fill tray directly underneath it such that a pill drop can be attempted without any spilling of pills.

If the current position is not the desired position, then at 1315, the robot 100 calculates the required X and Y coordinate offset to the desired position. Then a move command is given for the top pre-fill tray to move based on the calculated offset. Once it reaches a stop, then a reading is taken to determine if the top pre-fill tray 209 has reached its desired final position.

At 1317, if the new position after the move is the desired final position, i.e. also referred to as target position, then at 1319 the alignment between top pre-fill tray 209 and bottom pre-fill tray 211 is confirmed. However, if the new position is not the target or final position, then at 1321, the X and Y coordinate offset from the desired target position is calculated. Once again the command is given to the top pre-fill tray to move in the direction of the offset to reach its target position, which is the position that would align the top pre-fill tray 209 directly above the bottom pre-fill tray 211.

Several attempts may be made to move the top pre-fill tray 209 along the path to its final destination by either periodically assessing the position and distance from target or assessing the position each time the top pre-fill tray 209 stops moving. At 1323, the attempt counter, which is the Max try counter, is always checked to ensure that the number of attempts do not exceed the maximum allowable attempts. If they do, then an error message in 1309 is displayed.

The steps described in this flowchart provide for a feedback system in aligning the top per-fill tray with the bottom pre-fill tray. As described above, this feedback loop obtains positioning readings, checks number count, and feed this information back into the system to accurately displace the top and bottom pre-fill trays to their desired destinations.

FIG. 14 is a block diagram of a computer system that can is used in operation of the pill dispensing robot, according to some embodiments. The embodiments described herein, including systems, methods/processes, and/or apparatuses, may be implemented using well known servers/computers, such as computer 1400 shown in FIG. 14. For instance, elements of example pill dispensing robot 100, including any of computing devices or any elements thereof, each of the steps of described in FIGS. 2, 9, 10A-B, 11, and 13, and the functionality described in this document can each be implemented using one or more computers 1400.

Computer 1400 can be any commercially available and well-known computer capable of performing the functions described herein, such as computers available from International Business Machines, Apple, Sun, HP, Dell, Cray, etc. Computer 1400 may be any type of computer, including a desktop computer, a server, tablet PC, or mobile communication device, etc.

As shown in FIG. 14, computer 1400 includes one or more processors (e.g., central processing units (CPUs)), such as processor 1404. Processor 1404 may include any modules and/or layers of described in the Figures herein, and/or any portion or combination thereof, for example, though the scope of the embodiments is not limited in this respect. Processor 1404 is connected to a communication infrastructure 1402, such as a communication bus. In some embodiments, processor 1404 can simultaneously operate multiple computing threads.

Computer 1400 also includes a primary or main memory 1406, such as a random access memory (RAM). Main memory has stored therein control logic 828A (computer software), and data.

Computer 1400 also includes one or more secondary storage devices 1410. Secondary storage devices 1410 include, for example, a hard disk drive 1412 and/or a removable storage device or drive 1414, as well as other types of storage devices, such as memory cards and memory sticks. For instance, computer 1400 may include an industry standard interface, such as a universal serial bus (USB) interface for interfacing with devices such as a memory stick. Removable storage drive 1414 represents a floppy disk drive, a magnetic tape drive, a compact disk drive, an optical storage device, tape backup, etc.

Removable storage drive 1414 interacts with a removable storage unit 1416. Removable storage unit 1416 includes a computer useable or readable storage medium 1424 having stored therein computer software 1428B (control logic) and/or data. Removable storage unit 1416 represents a floppy disk, magnetic tape, compact disc (CD), digital versatile disc (DVD), Blue-ray disc, optical storage disk, memory stick, memory card, or any other computer data storage device. Removable storage drive 1414 reads from and/or writes to removable storage unit 1416 in a well-known manner.

Computer 1400 also includes input/output/display devices 1422, such as monitors, keyboards, pointing devices, etc. Computer 1400 further includes a communication or network interface 1420. Communication interface 1418 enables computer 1400 to communicate with mobile devices. For example, communication interface 1418 allows computer 1400 to communicate over communication networks or mediums 1422 (representing a form of a computer useable or readable medium), such as local area networks (LANs), wide area networks (WANs), the Internet, etc. Network interface 1420 may interface with remote sites or networks by using wired or wireless connections. Examples of communication interface 1418 include but are not limited to a modem, a network interface card (e.g., an Ethernet card), a communication port, a Personal Computer Memory Card International Association (PCMCIA) card, etc.

Control logic 1428C may be transmitted to and from computer 1400 by using the communication medium 1442. Any apparatus or manufacture comprising a computer useable or readable medium having control logic (software) stored therein is referred to herein as a computer program product or program storage device. This includes, but is not limited to, computer 1400, main memory 1406, secondary storage devices 1410, and removable storage unit 1416. Such computer program products, having control logic stored therein that, when executed by one or more data processing devices, because such data processing devices to operate as described herein, represent embodiments of the invention. For example, Control logic 1428C may be used to align the top pre-fill tray with the bottom pre-fill tray and in the process take readings, provide feedback, and direct the hardware component to move in the desired direction to ensure alignment. Additionally, the control logic 1428C may be used in any of the flowcharts or operations that require a decision-making step before dispensing the pills to the next stage.

Although the present invention has been described in connection with several embodiments, the invention is not intended to be limited to the specific forms set forth herein. On the contrary, it is intended to cover such alternatives, modifications, and equivalents as can be reasonably included within the scope of the invention as defined by the appended claims.

What is claimed is:

1. A method of dispensing pills from an automated pill dispensing robot, the method comprising: dispensing a plurality of pills from a storage module, wherein the plurality of pills are designated for a specific patient in accordance to a prescription plan; receiving the plurality of pills dispensed from the storage module into a hopper system; aligning the hopper system with a top pre-fill tray and dispensing the plurality of pills from the hopper system into the top pre-fill tray upon completion of alignment; aligning the top pre-fill tray with a bottom pre-fill tray, wherein the alignment includes g) establishing an XY coordinate plane, h) assigning an X and Y coordinate position of (0, 0) as the initial starting position of the top pre-fill tray, i) assigning an X and Y coordinate position of (0, 0) as the initial starting position of the bottom pre-fill tray, j) measuring the distance between the initial starting position of (0, 0) to the current X and Y coordinate position of the top pre-fill tray, k) measuring the distance between the initial starting position of (0, 0) to the current X and Y coordinate position of the bottom pre-fill tray, and l) displacing the bottom pre-fill tray to the same current X and Y coordinates of the top-prefill tray such that, once displaced, the bottom pre-fill tray is aligned directly underneath the top pre-fill tray with the same X and Y coordinates, wherein both the top pre-fill tray and the bottom pre-fill tray are housed inside the dispensing section of the pill dispensing robot such that the top pre-fill tray and the bottom pre-fill tray can move independently from one another in an X or Y direction; dispensing the plurality of pills from the top pre-fill tray into the bottom pre-fill tray upon completion of alignment between top pre-fill tray and the bottom pre-fill tray; aligning the bottom pre-fill tray with a desired pill pack located in the packing plate; and verifying the pill pack located in the packing plate to ensure that the plurality of pills dispensed from the storage module match the pill pack that is designated for the specific patient, wherein aligning the hopper system with a top pre-fill tray comprises: using a hopper system, wherein the hopper system includes a hopper having a wider opening at its top and narrower opening at its bottom, the hopper's narrower bottom opening is square in shape and includes a plurality of photo sensors, using a pre-fill tray that includes a plurality of slots that are placed in a plurality of rows and columns, wherein a common wall shared between each row of slots includes a plurality of X-direction pointers and a common wall shared between each column of slots includes a plurality of Y-direction pointers; wherein the hopper's narrow square shaped opening matches the size and shape of a slot in the top pre-fill tray; obtaining the X and Y coordinates of the current location of a desired slot in the top-pre-fill tray; measuring the displacement required to align the desired slot in the top-pre-fill tray with the square shaped narrower bottom opening in the hopper; displacing the top pre-fill tray such that the desired slot is directly underneath the square shaped narrower bottom opening of the hopper; and confirming alignment of the hopper with the desired slot in the top pre-fill tray, wherein confirming alignment includes reading the X and Y direction pointers coordinates of the slot underneath the square shaped narrower bottom opening in the hopper, wherein said reading of the X and Y direction pointers coordinates being performed by the plurality of photo sensors located in the square shaped narrower bottom opening in the hopper.

2. The method of claim 1, wherein aligning the top pre-fill tray with a bottom pre-fill tray comprises:
determining the number of displacement attempts made to align the top pre-fill tray with the bottom pre-fill tray; and
displacing the bottom pre-fill tray in the desired direction of alignment if the number of alignment attempts made have not reached a pre-set maximum number of alignment attempts allowed.

3. The method of claim 2, further comprising, ending the alignment process and displaying an error message if the number of attempts made exceed the pre-set maximum number of attempts allowed.

4. The method of claim 1, wherein verifying the pill pack located in the packing plate further comprises:
using a packing plate that includes a radio frequency identification (RFID) reader, wherein the packing plate includes a plurality of slots capable of receiving a pill pack;
using a pill pack that includes an RFID tag, wherein the RFID tag holds information specific to a particular patient;
reading the RFID tag on the pill pack using the RFID reader on the packing plate to obtain information associated with the RFID tag; and
using the information obtained from the RFID tag to query a database and determining whether the RFID tag is associated with a new pill pack or an RFID tag that is associated with an old pill pack or a separate patient; and
signaling the bottom pre-fill tray to drop a plurality of pills into the pill pack if the querying results confirm that it is a new pill pack.

5. The method of claim 1, further comprising parallel processing of a plurality of pill packs at a time, wherein the dispensing system is capable of dispensing the pills designated for a first pill pack and subsequently dispensing the pills designated for a second pill pack without having to wait for the completion of first pill pack by utilizing the mechanisms provided by the plurality of pre-fill trays that allow for separation of pills designated for the first pill pack from the pills designated for the second pill pack.

6. A system for dispensing a plurality of pills using an automated robot comprising: one or more processors; and a control module executable by the one or more processors, wherein, the control module is configured to execute the steps of: dispensing a plurality of pills from a storage module, wherein the plurality of pills are designated for a specific patient in accordance to a prescription plan; receiving the plurality of pills dispensed from the storage module into a hopper system; aligning the hopper system with a top pre-fill tray and dispensing the plurality of pills from the hopper system into the top pre-fill tray upon completion of alignment; aligning the top pre-fill tray with a bottom pre-fill tray, wherein the alignment includes: a) establishing an XY coordinate plane, b) assigning an X and Y coordinate position of (0, 0) as the initial starting position of the top pre-fill tray, c) assigning an X and Y coordinate position of (0, 0) as the initial starting position of the bottom pre-fill tray, d) measuring the distance between the initial starting position of (0, 0) to the current X and Y coordinate position of the top pre-fill tray, e) measuring the distance between the initial starting position of (0, 0) to the current X and Y coordinate position of the bottom pre-fill tray, and f) displacing the bottom pre-fill tray to the same current X and Y coordinates of the top-prefill tray such that, once displaced, the bottom pre-fill tray is aligned directly underneath the top pre-fill tray with the same X and Y coordinates, wherein both the top pre-fill tray and the bottom pre-fill tray are housed inside the dispensing section of the pill dispensing robot such that the top pre-fill tray and the bottom pre-fill tray can move independently from one another in an X or Y direction; dispensing the plurality of pills from the top pre-fill tray into the bottom pre-fill tray upon completion of alignment between top pre-fill tray and the bottom pre-fill tray; aligning the bottom pre-fill tray with a desired pill pack located in the packing plate; and verifying the pill pack located in the packing plate to ensure that the plurality of pills dispensed from the storage module match the pill pack that is designated for the specific patient, wherein verifying the pill pack located in the packing plate further comprises: using a packing plate that includes a radio frequency identification (RFID) reader, wherein the packing plate includes a plurality of slots capable of receiving a pill pack; using a pill pack that includes an RFID tag, wherein the RFID tag holds information specific to a particular patient; reading the RFID tag on the pill pack using the RFID reader on the packing plate to obtain information associated with the RFID tag; using the information obtained from the RFID tag to query a database and determine whether the RFID tag is associated with a new pill pack or an RFID tag that is associated with an old pill pack or a separate patient; and signaling the bottom pre-fill tray to drop a plurality of pills into the pill pack if the querying results confirm that it is a new pill pack.

7. The system of claim 6, wherein aligning the top pre-fill tray with a bottom pre-fill tray comprises:
determining the number of displacement attempts made to align the top pre-fill tray with the bottom pre-fill tray; and
displacing the bottom pre-fill tray in the desired direction of alignment if the number of alignment attempts made have not reached a pre-set maximum number of alignment attempts allowed.

8. The system of claim 6, wherein aligning the hopper system with a top pre-fill tray comprises:
using a hopper system, wherein the hopper system includes a hopper having a wider opening at its top and narrower opening at its bottom, the hopper system's narrower bottom opening is square in shape and includes a plurality of photo sensors,
using a hopper system, wherein the hopper system includes a hopper having a wider opening at its top and narrower opening at its bottom, the hopper's narrower bottom opening is square in shape and includes a plurality of photo sensors,
using a pre-fill tray that includes a plurality of slots that are placed in a plurality of rows and columns, wherein a common wall shared between each row of slots includes a plurality of X-direction pointers and a common wall shared between each column of slots includes a plurality of Y-direction pointers; wherein the hopper's narrow square shaped opening matches the size and shape of a slot in the top pre-fill tray;
obtaining the X and Y coordinates of the current location of a desired slot in the top-pre-fill tray;
measuring the displacement required to align the desired slot in the top-pre-fill tray with the square shaped narrower bottom opening in the hopper;
displacing the top pre-fill tray such that the desired slot is directly underneath the square shaped narrower bottom opening of the hopper; and
confirming alignment of the hopper with the desired slot in the top pre-fill tray.

9. A system for dispensing a plurality of pills using an automated robot comprising:
one or more processors; and
a control module executable by the one or more processors, wherein, the control module is configured to execute the steps of:
dispensing a plurality of pills from a storage module, wherein the plurality of pills are designated for a specific patient in accordance to a prescription plan;
receiving the plurality of pills dispensed from the storage module into a hopper system;
aligning the hopper system with a top pre-fill tray and dispensing the plurality of pills from the hopper system into the top pre-fill tray upon completion of alignment;
aligning the top pre-fill tray with a bottom pre-fill tray, wherein the alignment includes
a) establishing an XY coordinate plane,
b) assigning an X and Y coordinate position of (0, 0) as the initial starting position of the top pre-fill tray,
c) assigning an X and Y coordinate position of (0, 0) as the initial starting position of the bottom pre-fill tray,
d) measuring the distance between the initial starting position of (0, 0) to the current X and Y coordinate position of the top pre-fill tray,
e) measuring the distance between the initial starting position of (0, 0) to the current X and Y coordinate position of the bottom pre-fill tray, and
f) displacing the bottom pre-fill tray to the same current X and Y coordinates of the top-prefill tray such that, once displaced, the bottom pre-fill tray is aligned directly underneath the top pre-fill tray with the same X and Y coordinates, wherein both the top pre-fill tray and the bottom pre-fill tray are housed inside the dispensing section of the pill dispensing robot such that the top pre-fill tray and the bottom pre-fill tray can move independently from one another in an X or Y direction;
dispensing the plurality of pills from the top pre-fill tray into the bottom pre-fill tray upon completion of alignment between top pre-fill tray and the bottom pre-fill tray;
aligning the bottom pre-fill tray with a desired pill pack located in the packing plate; and
verifying the pill pack located in the packing plate to ensure that the plurality of pills dispensed from the storage module match the pill pack that is designated for the specific patient, wherein verifying the pill pack located in the packing plate further comprises:
using a packing plate that includes a radio frequency identification (RFID) reader, wherein the packing plate includes a plurality of slots capable of receiving a pill pack;
using a pill pack that includes an RFID tag, wherein the RFID tag holds information specific to a particular patient;
reading the RFID tag on the pill pack using the RFID reader on the packing plate to obtain information associated with the RFID tag;
using the information obtained from the RFID tag to query a database and determining whether the RFID tag is associated with a new pill pack or an RFID tag that is associated with an old pill pack or a separate patient; and signaling the bottom pre-fill tray to drop a plurality of pills into the pill pack if the querying results confirm that it is a new pill pack.

* * * * *